United States Patent [19]  [11] Patent Number: 5,068,419
Kulprathipanja et al.  [45] Date of Patent: Nov. 26, 1991

[54] SEPARATION OF AN ORGANIC ACID FROM A FERMENTATION BROTH WITH AN ANIONIC POLYMERIC ADSORBENT

[75] Inventors: Santi Kulprathipanja, Inverness; Anil R. Oroskar, Downers Grove, both of Ill.

[73] Assignee: UOP, Des Plaines, Ill.

[21] Appl. No.: 349,273

[22] Filed: May 8, 1989

Related U.S. Application Data

[63] Continuation-in-part of Ser. No. 121,830, Nov. 16, 1987, Pat. No. 4,851,573, and a continuation-in-part of Ser. No. 122,161, Nov. 16, 1987, Pat. No. 4,851,574, each is a continuation-in-part of Ser. No. 943,219, Dec. 18, 1986, Pat. No. 4,720,579.

[51] Int. Cl.$^5$ ............................................. C07C 51/42
[52] U.S. Cl. .................................................... 562/580
[58] Field of Search ........................................ 562/580

[56] References Cited

U.S. PATENT DOCUMENTS

| | | | |
|---|---|---|---|
| 2,697,725 | 12/1954 | Bryce | 260/527 |
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,706,812 | 12/1972 | De Rosset et al. | 269/674 SA |
| 3,983,170 | 9/1976 | Sumikawa et al. | 260/535 |
| 4,031,038 | 6/1977 | Grinstead et al. | 260/2.2 R |
| 4,098,867 | 7/1978 | Grinstead et al. | 423/24 |
| 4,323,702 | 4/1982 | Kawabata et al. | 562/485 |
| 4,552,905 | 11/1985 | Keil et al. | 521/149 |
| 4,642,397 | 2/1987 | Zinnen et al. | 568/934 |

FOREIGN PATENT DOCUMENTS 868926 6/1957 United Kingdom .

Primary Examiner—Paul J. Killos
Attorney, Agent, or Firm—Thomas K. McBride; John F. Spears, Jr.; Jack H. Hall

[57] ABSTRACT

An organic acid is separated from a fermentation broth by using an adsorbent comprising a water-insoluble macroreticular or gel weakly basic anionic exchange resin possessing tertiary amine or pyridine functional groups or a strongly basic anionic exchange resin possessing quaternary amine functional groups. The resins are in sulfate form and have a cross-linked acrylic or styrene resin matrix. The organic acid is desorbed with water or dilute inorganic acid, e.g., sulfuric. The pH of the feed is maintained below the first ionization constant (pKa$_1$) of the organic acid to obtain high selectivity.

13 Claims, 13 Drawing Sheets

SEPARATION OF AN ORGANIC ACID FROM A FERMENTATION BROTH WITH AN ANIONIC POLYMERIC ADSORBENT

CROSS-REFERENCE TO RELATED APPLICATIONS

This application is a continuation-in-part of pending applications Ser. No. 121,830, filed Nov. 16, 1987, now U.S. Pat. No. 4,851,573 for Separation of Citric Acid From Fermentation Broth with a Weakly Basic Anionic Exchange Resin Adsorbent and Ser. No. 122,161 filed Nov. 16, 1987, now U.S. Pat. No. 4,851,574 for Separation of Citric Acid From Fermentation Broth With a Strongly Basic Anionic Exchange Resin Adsorbent, both of which are continuations-in-part of Ser. No. 943,219 filed Dec. 18, 1986, now U.S. Pat. No. 4,720,579.

FIELD OF THE INVENTION

The field of art to which this invention pertains is the solid bed adsorptive separation of organic acids from fermentation broths containing the organic acid which may additionally contain other organic acids, carbohydrates, amino acids, ethanol, proteins and salts. More specifically, the invention relates to a process for separating an organic acid from fermentation broths containing same which process employs a non-zeolite polymeric adsorbent, which selectively adsorbs the organic acid and comprises a weakly basic anionic exchange resin possessing tertiary amine or pyridine functional groups, or a strongly basic anionic exchange resin possessing quaternary amine functional groups and mixtures thereof.

BACKGROUND OF THE INVENTION

Organic acids, e.g., lactic acid, citric acid, etc., are used as food acidulants and in pharmaceutical, industrial and detergent formulations. The increased popularity of liquid detergents, foods and pharmaceuticals formulated with organic acids has been primarily responsible for growth of worldwide production in excess of 1 billion pounds per year which is expected to continue in the future.

Citric acid is produced by a submerged culture fermentation process which employs molasses as feed and the microorganism, Aspergillus Niger. The fermentation product will contain carbohydrates, amino acids, proteins, and salts as well as citric acid, which must be separated from the fermentation broth.

Lactic acid is produced by a submerged culture fermentation process which employs molasses, potatoes or starch as feed and a microorganism, e.g., Lactobacillus del brueckii, L. bulgarcius or L. leichnanii. The fermentation product will contain carbohydrates, amino acids, proteins and salts as well as lactic acid, which must be separated from the fermentation broth.

Other acids may be produced by fermentation processes, including aconitic acid, glutamic acid and tartaric acid, and others listed in Biotechnology, Vol. 3, Chap. 3, Edited by Rehm and Reed (1983) pages 387–478, all of which are mono-, di- or polycarboxylic acids.

Technology currently employed for the separation of organic acids generally involve calcium salt precipitation of the acid. The resulting calcium salt can be filtered and acidified with sulfuric acid to regenerate the acid. In another process for separating citric acid, the acid is extracted from the fermentation broth with a mixture of trilauryl-amine, n-octanol and a $C_{10}$ or $C_{11}$ isoparaffin. Citric acid is reextracted from the solvent phase into water with the addition of heat. Both techniques, however, are complex, expensive and they generate a substantial amount of waste for disposal.

European Patent No. 135,728 discloses the separation of lactic acid from a fermentation medium with an adsorbent comprising a polymer with tertiary amino group described in U.S. Pat. No. 4,552,905. The resins are not disclosed to be in sulfate form, as applicants have herein disclosed their invention. Furthermore, the adsorbed acid is eluted with a solvent such as methanol.

U.K. Patent No. 868,926 relates to the purification and concentration of a carboxylic acid by an ion exchange mechanism using an ion exchange resin in $OH^-$ form. After recovery of the acid by exchange with sulfurous acid, the resin is regenerated with hot water to convert the resin back to $OH^-$ form.

U.S. Pat. No. 4,323,702 discloses the separation of carboxylic acids from a synthesis mixture with strong and weakly basic anionic exchange resins in $OH^-$ form, using an organic solvent, e.g. alcohol, ketone or ester as a desorbent.

The invention herein can be practiced in fixed or moving adsorbent bed systems by batch or continuous processes, but the preferred system for this separation is a continuous countercurrent simulated moving bed system, such as described in Broughton U.S. Pat. Nos. 2,985,589, incorporated herein by reference. Cyclic advancement of the input and output streams can be accomplished by a manifolding system, which are also known, e.g., by rotary disc valves shown in U.S. Pat. No. 3,040,777 and 3,422,848. Flow rates in the various zones may be set and regulated by a programmed flow controller. Equipment utilizing these principles are familiar, in sizes ranging from pilot plant scale (deRosset U.S. Pat. No. 3,706,812) to commercial scale with flow rates from a few cc per hour to many thousands of gallons per hour.

The functions and properties of adsorbents and desorbents in the chromatographic separation of liquid components are well known, but for reference thereto, Zinnen et al U.S. Pat. No. 4,642,397 is incorporated herein.

The present method makes it possible to separate the organic acid in a single adsorption step and to recover the organic acid from the adsorbent to obtain the purified organic acid using an easily separated desorbent.

SUMMARY OF THE INVENTION

This invention relates to a process for adsorbing an organic acid from a fermentation broth onto a polymeric adsorbent in sulfate form ($SO_4^=$) comprising a weakly basic anionic exchange resin possessing tertiary amine or pyridine functional groups, or a strongly basic anionic exchange resin possessing quaternary amine functional groups and mixtures thereof and thereafter recovering the organic acid by desorption thereof with a suitable desorbent under desorption conditions. One condition for the practice of the invention that is required for achieving high selectivity is to maintain the pH of the feed solution, and thereby the adsorption zone, lower than the first ionization constant ($pKa_1$) of the acid or the pKa of a monocarboxylic acid such as lactic acid.

In the preferred practice of the invention, the organic acid is separated from a feed mixture comprising a fermentation broth containing same in a continuous, countercurrent simulated moving bed chromatographic process, which process employs a polymeric adsorbent comprising a weakly basic anionic exchange resin possessing tertiary amine or pyridine functional groups or a strongly basic anionic exchange resin possessing quaternary amine functional groups and mixtures thereof which comprises the steps of:

(a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent located between a feed input stream at an upstream boundary of said zone and a raffinate output stream at a downstream boundary of said zone;

(c) maintaining a purification zone immediately upstream from said adsorption zone, said purification zone defined by the adsorbent located between an extract output stream at an upstream boundary of said purification zone and said feed input stream at a downstream boundary of said purification zone;

(d) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed mixture at a pH below the ionization constant ($pKa_1$) for said acid into said adsorption zone at adsorption conditions to effect the selective adsorption of said acid by said adsorbent in said adsorption zone and withdrawing a raffinate output stream comprising the nonadsorbed components of said fermentation broth from said adsorption zone;

(f) passing a desorbent material into said desorption zone at desorption conditions to effect the displacement of said acid from the adsorbent in said desorption zone;

(g) withdrawing an extract output stream comprising said acid and desorbent material from said desorption zone;

(h) passing at least a portion of said extract output stream to a separation means and therein separating at separation conditions at least a portion of said desporbent material; and, (i) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams. At least a portion of said raffinate output stream may be passed to a separation means, at separation conditions, thereby separating at least a portion of said desorbent material, to produce a raffinate product having a reduced concentration of desorbent material. Further, a buffer zone may be maintained immediately upstream from said desorption zone, said buffer zone defined as the adsorbent located between the desorbent input stream at a downstream boundary of said buffer zone and the raffinate output stream at an upstream boundary of said buffer zone.

Other aspects of the invention encompass details of feed mixtures, adsorbents, desorbents and operating conditions which are hereinafter disclosed.

DESCRIPTION OF THE INVENTION

Figure 1:
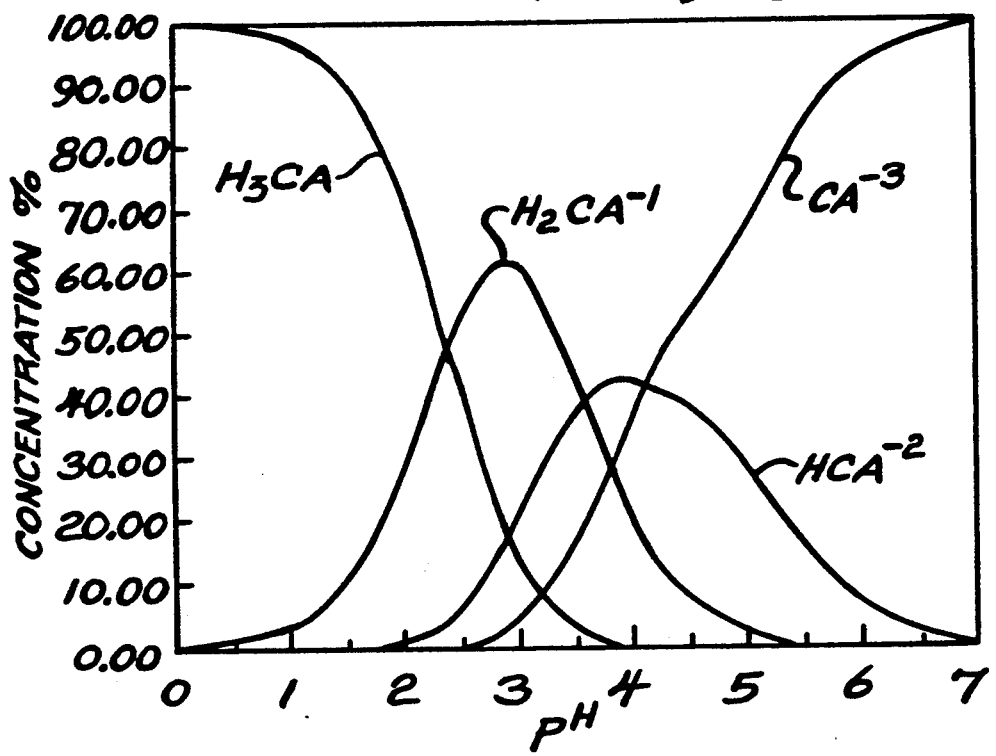
FIG. 1 is the plot of concentration of various citric acid species versus the pH of citric acid dissociation which shows the shifting of the equilibrium point of the citric acid dissociation by varying the concentration of citric acid, citrate anions and the hydrogen ion.

At the outset the definitions of various terms used throughout the specification will be useful in making clear the operation, objects and advantages of the instant process.

A "feed mixture" is a mixture containing one or more extract components and one or more raffinate components to be separated by the present process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process, citric acid is an extract component and salts and carbohydrates are raffinate components. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity, organic acid product at high recoveries, it will be appreciated that an extract component is never completely adsorbed by the adsorbent. Likewise, a raffinate component is completely nonadsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of the organic acid to that of the less selectively adsorbed components will be lowest in the raffinate stream, next highest in the feed mixture, and the highest in the extract stream. Likewise, the ratio of the concentration of the less selectively adsorbed components to that of the more selectively adsorbed organic acid will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "nonselective void volume" of the adsorbent is the volume of the adsorbent which does not selectively retain an extract component from the feed mixture. This volume includes the cavities of the adsorbent which contain no adsorptive sites and the interstitial void spaces between adsorptive particles. The selective pore volume and the nonselective void volume are generally expressed in volumetric quantities and are of importance in determining the proper flow rates of fluid required to be passed into an operational zone for efficient operations to take place for a given quantity of adsorbent. When adsorbent "passes" into an operational zone of a continuous countercurrent simulated moving bed process, its nonselective void volume together with its selective pore volume carries fluid into that zone. The nonselective void volume is utilized in determining the amount of fluid which should pass into the same zone in a countercurrent direction to the adsorbent to displace the fluid present in the nonselective void volume. If the fluid flow rate passing into a zone is smaller than the nonselective void volume rate of the adsorbent material passing into that zone, there is a net entrainment of liquid into the zone by the adsorbent. Since this net entrainment is a fluid present in nonselective void volume of the adsorbent, it in most instances comprises less selectively retained feed components. The selective pore volume of an adsorbent can, in certain instances, adsorb portions of raffinate material from the fluid surrounding the adsorbent since, in certain instances, there is competition between extract material and raffinate material for adsorptive sites within the selective pore volume. If a large quantity of raffinate material with respect to extract material surrounds the adsorbent, raffinate material can be competitive enough to be adsorbed by the adsorbent.

The feed material contemplated in this invention is the fermentation product obtained from the submerged culture fermentation of molasses, by any one of a number of microorganisms known to be effective for converting the carbohydrate source to an acid. For example, one feed material contemplated in this invention is the fermentation product, comprising lactic acid, obtained from the submerged culture fermentation of molasses, potatoes or, especially, starch by one of the microorganism, *Lactobacillus del brueckii, L. bulgarcius* or *L. leichnanii*. The fermentation product will have a composition exemplified by the following:

|  | wt. % (dry) |  |
|---|---|---|
| Lactic acid | 57.14 | (9.44 wt. % wet basis) |
| Salts and DP3 | 32.90 | |
| Acetic acid | 1.74 | |
| Other Carbohydrates (Dextrose & Unknowns B1) | 2.58 | |
| Ethanol | 0.242 | |
| Unknowns (A2) | 2.73 | |
| Unknowns (A1) | 1.16 | |
| Unknowns not analyzed | bal. | |

The salts may include K, Na, Ca, Mg and P. The unknowns may include, other than dextrose and DP3, DP2, other unidentified saccharides, amino acids and proteins. The composition of the feedstock may vary from that given above and still be used in the invention.

Another feed material contemplated is the fermentation product, comprising citric acid, obtained from the submerged culture fermentation of molasses by the microorganism, Aspergillus Niger. The fermentation product will have a composition exemplified by the following:

| Citric acid | 12.9% ± 3% |
|---|---|
| Salts | 6,000 ppm |
| Carbohydrates (sugars) | 1% |
| Others (proteins and amino acids) | 5% |

The salts will be K, Na, Ca, Mg and Fe. The carbohydrates are sugars including glucose, xylose, mannose, oligosaccharides of DP2 and DP3 plus as many as 12 or more unidentified saccharides. The composition of the feedstock may vary from that given above and still be used in the invention. However, juices, such as citrus fruit juices, are not acceptable or contemplated because other materials contained therein will be adsorbed at the same time rather than citric acid alone. Johnson, J., *Sci Food Agric.*, Vol. 33 (3) pp 287-93.

The separation of citric acid can be enhanced significantly by adjusting the pH of the feed to a level below the first ionization constant of citric acid. The first ionization constant ($pKa_1$) of citric acid is 3.13, *Handbook of*

Chemistry & Physics), 53rd Edition, 1972-3, CRC press, pp D-120 and 121 and, therefore, the pH of the citric acid feed should be below 3.13. When the pH for a 13% concentrated solution of citric acid is 2.4 or greater, for example, as in FIG. 3A (Example I) of said U.S. Pat. No. 4,720,579, citric acid "breaks through" (is desorbed) with the salts and carbohydrates at the beginning of the cycle, indicating that all the citric acid is not adsorbed. In contrast, less "break through" of citric acid is observed when the pH is 1.7 and no "break through" when the pH is 0.9 at the 13% level, for example, as in FIGS. 3B and 3C, respectively, of said U.S. Pat. No. 4,720,579.

In aqueous solution, unionized citric acid exists in equilibrium with the several citrate anions and hydrogen ions. This is shown in the following equations, where the acid dissociation constants $pKa_1$, $pKa_2$ and $pKa_3$ of citric acid at 25° C. are 3.13, 4.74 and 5.40, respectively:

Equation 1

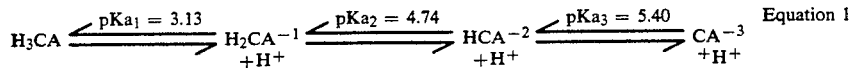

Equation 1

The equilibrium point of citric acid dissociation can be shifted by varying the concentrations of citric acid, the citrate anion or the hydrogen ion. This is demonstrated in FIG. 1, for the concentration of the several citric acid species in solution versus pH at 90° C. The result shows a higher percent of nonionized citric acid ($H_3CA$) at a higher hydrogen ion concentration (lower pH). Decreasing the pH (raising the $H^+$ ion concentration) will introduce more nonionized citric acid while reducing the citrate anionic species ($H_2CA^{-1}$, $HCA^{-2}$ and $CA^{-3}$) in the solution.

Likewise, the separation of other organic acids can be enhanced significantly by adjusting the pH of the feed to a level below the first ionization constant of the acid. For example, the (only) ionization constant (pKa) of lactic acid is 3.86 and, therefore, the pH of a lactic acid feed and the adsorption zone should be below 3.86. Others are given in *The Handbook of Chemistry & Physics, supra*.

The same equilibrium established above for citric acid can be demonstrated for other acids, e.g., unionized lactic acid exists in equilibrium in aqueous solution with lactate anions and hydrogen ions. This is shown in the following equation where the acid dissociation constant, pKa of lactic acid at 100° C. is 3.86.

Equation 2

Equation 2

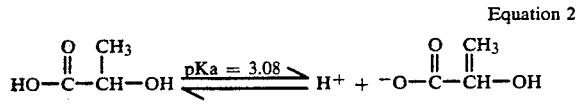

The equilibrium point of lactic acid dissociation can be shifted by varying the concentration of lactic acid, the lactate anion or the hydrogen ion.

Based on the equilibrium equation and the resin properties mentioned above, the nonionized acids will be separated from other ionic species (including the acid anions) in the fermentation broths using the resin adsorbents described. However, the lower the pH of the solution, the greater the acid recovery. Without the intention of being limited by this explanation, it appears that the nonionic acid species in the solution is preferentially adsorbed on the adsorbents of the present invention either through an acid-base interaction mechanism or a hydrogen bonding mechanism or a mechanism based on a strong affinity for relatively hydrophobic species or a combination of these mechanisms.

Desorbent material used in various prior art adsorptive separation processes can vary depending upon such factors as the type of operation employed. In the swing bed system, in which the selectively adsorbed feed component is removed from the adsorbent by a purge stream, desorbent selection is not critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to ensure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high, nor would the desorbent material be available for reuse in the process. It is therefore contemplated that any desorbent material used in this process will preferably have a substantially different average boiling point than that of the feed mixture to allow separation of at least a portion of the desorbent material from feed components in the extract and raffinate streams by simple fractional distillation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Finally, desorbent materials should also be materials which are readily available and therefore reasonable in cost. In the preferred isothermal, isobaric, liquid phase operation of the process of the present invention, it has been found that water or dilute, inorganic acids are particularly effective desorbent materials.

Aqueous solutions of sulfuric acid, nitric acid, hydrochloric acid, phosphoric acid and mixtures thereof can be used in amounts corresponding to 0.002 to 1.0N (normal), with best results obtained with dilute sulfuric acid between 0.01 to 0.2N.

The prior art has also recognized that certain characteristics of adsorbents are highly desirable, if not absolutely necessary, to the successful operation of a selective adsorption process. Such characteristics are equally important to this process. Among such characteristics are: (1) adsorptive capacity for some volume of an extract component per volume of adsorbent; (2) the selective adsorption of an extract component with respect to a raffinate component and the desorbent material; and (3) sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component, the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity for one component as compared to another component. Relative selectivity can be expressed not only for one feed component as compared to another, but can also be expressed between any feed mixture component and the desorbent material. The selectivity, $\beta$, as used throughout this specification is defined as the ratio of the two components of the adsorbed phase over the ratio of the same two components in the unadsorbed phase at equilibrium conditions. Relative selectivity is shown as Equation 3 below:

Equation 3

$$\text{Selectivity} = \beta = \frac{[\text{vol. percent } C/\text{vol. percent } D]_A}{[\text{vol. percent } C/\text{vol. percent } D]_U} \quad \text{Equation 3}$$

where C and D are two components of the feed represented in volume percent and the subscripts A and U represent the adsorbed and unadsorbed phases respectively. The equilibrium conditions were determined when the feed passing over a bed of adsorbents did not change composition after contacting the bed of adsorbent. In other words, there was no net transfer of material occurring between the unadsorbed and the adsorbed phases. Where selectivity of two components approaches 1.0 there is no preferential adsorption of one component by the adsorbent with respect to the other; they are both adsorbed (or nonadsorbed) to about the same degree with respect to each other. As the $\beta$ becomes less than or greater than 1.0 there is a preferential adsorption by the adsorbent for one component with respect to the other. When comparing the selectivity by the adsorbent of one component C over component D, a $\beta$ larger than 1.0 indicates preferential adsorption of component C within the adsorbent. A $\beta$ less than 1.0 would indicate that component D is preferentially adsorbed leaving an unadsorbed phase richer in component C and an adsorbed phase richer in component D. Ideally desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity, the easier the separation is to perform. Higher selectivities permit a smaller amount of adsorbent to be used. The third important characteristic is the exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

Resolution is a measure of the degree of separation of a two-component system, and can assist in quantifying the effectiveness of a particular combination of adsorbent, desorbent, conditions, etc., for a particular separation. Resolution for purposes of this application is defined as the distance between the two peak centers divided by the average width of the peaks at $\frac{1}{2}$ the peak height as determined by the pulse tests described hereinafter. The equation for calculating resolution is thus:

Equation 4

$$R = \frac{L_2 - L_1}{1/2 \, (W_1 + W_2)} \quad \text{Equation 4}$$

where $L_1$ and $L_2$ are the distances, in ml, from a reference point, e.g., zero or the void volume, to the centers of the peaks of the respective components and $W_1$ and $W_2$ are the widths of the peaks at $\frac{1}{2}$ the height of the peaks. The value of the resolution may have little significance where the concentration of components is low, since it is extremely difficult to determine the location of peak of the envelope and therefore, its retention volume, and also the width at one-half the peak height. In the present Examples VIII-X relating to lactic acid separation, this situation exists as to the impurity groups (A1, A2 and B2) and, therefore, although the resolution values are set forth in the examples, the values are not necessarily deemed to be of significance in assessing the separation.

The resins of the invention can be gellular (or "gel-type") or "macroreticular" as the term is used in some recent literature, namely, Kunin and Hetherington, *A Progress Report on the Removal of Colloids From Water by Macroreticular Ion Exchange Resins*, paper presented at the International Water Conference, Pittsburgh, Pa., October 1969, reprinted by Rohm & Haas Co. In recent adsorption technology, "the term microreticular refers to the gel structure per se, size of the pores which are of atomic dimensions and depend upon the swelling properties of the gel" while "macroreticular pores and true porosity refer to structures in which the pores are larger than atomic distances and are not part of the gel structure. Their size and shape are not greatly influenced by changes in the environmental conditions such as those that result in osmotic pressure variations" while the dimensions of gel structure are "markedly dependent upon the environmental conditions." In "classical adsorption", "the terms microporous and macroporous normally refer to those pores less than 20 A and greater than 200 A, respectively. Pores of diameters between 20 A and 200 A are referred to as transitional pores." The authors selected the term "macroreticular", instead, to apply to the new ion exchange resins used in this invention, which "have both a microreticular as well as a macroreticular pore structure. The former refers to the distances between the chains and crosslinks of the swollen gel structure and the latter to the pores that are not part of the actual chemical structure. The macroreticular portion of structure may actually consist of micro-, macro-, and transitional-pores depending upon the pore size distribution." (Quotes are from page 1 of the Kunin et al. article). The macroreticular structured adsorbents also have good resistance to attrition (not common to conventional macroreticular resins). In this application, therefore, all reference to "macroreticular" indicates adsorbent of the types described above having the dual porosity defined by Kunin and Hetherington. "Gel" and "gel-type" are used in their conventional sense.

One class of adsorbents to be used in the process of this invention will comprise weakly basic anion exchange resins possessing tertiary amine or pyridine functionality in sulfate form in a cross-linked polymeric matrix, e.g., acrylic or styrene. They are especially suitable when produced in bead form, have a high degree of uniform polymeric porosity, exhibit chemical and physical stability and good resistance to attrition.

Further, looking at both the tertiary amine- and pyridine-function-containing ion exchange resins of the present invention, the lone pair electron from the nitrogen atom can hydrogen bond to the acid through the sulfate ion, as, for example, with a tertiary amine function-containing resin:

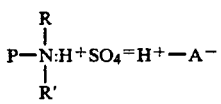

(1)

and with a pyridine function-containing resin:

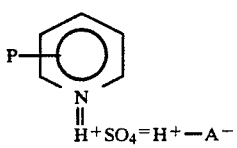

(2)

where
P=resinous moiety
R,R'=lower alkyl, $C_{1-3}$

A=Organic acid anion

In a feed with the pH higher than the first ionization constant, $pKa_1$, there will be insufficient hydrogen ions for the hydrogen bond formation with the sulfate ion; the acid will not be adsorbed by the resin and will "break through" with salts and carbohydrates at the beginning of the cycle.

Adsorbents such as just described are normally available as the chloride, but can be converted to the sulfate form by the process described hereinafter. "Amberlite" adsorbent resins, manufactured by the Rohm and Haas Company, are suitable and those known to be effective for use by this invention include Amberlite adsorbents XE-275 (IRA-35) and IRA-68, described in Rohm and Haas Company literature as "insoluble in all common solvents and having open structure for effective adsorption and desorption of large molecules without loss of capacity, due to organic fouling." Also suitable are AG3-X4A and AG4-X4 manufactured by Bio Rad and comparable resins sold by Dow Chemical Co., such as Dowex66, and Dow experimental resins made in accordance with U.S. Pat. Nos. 4,031,038 and 4,098,867.

The available weakly basic polymeric adsorbents of this class will differ somewhat in physical properties such as porosity (volume percent), skeletal density and nominal mesh sizes, and perhaps more so in surface area, average pore diameter and dipole moment. The preferred adsorbents will have a surface area of 10–2000 square meters per gram and preferably from 100–1000 $m^2/g$. Specific properties of the materials listed above can be found in company literature and technical brochures, such as those in the following Table 1 which are incorporated herein by reference. Others of the general class are also available.

TABLE 1

| | Weakly Basic Anionic Exchange Resins | |
|---|---|---|
| Adsorbent | Matrix Type | Reference to Company Literature |
| AG3-4A (Bio Rad) | Polystyrene | Chromatography Electrophoresis Immunochemistry Molecular Biology-HPLC-Price List M April 1987 (Bio-Rad) |
| AG4-X4 | Acrylic | Chromatography Electrophoresis Immunochemistry Molecular Biology-HPLC-Price List M April 1987 (Bio-Rad) |
| Dow Experimental Resins | Polystyrene | U.S. Pat. Nos. 4,031,038 and 4,098,867 |
| Dowex 66 | Polystyrene | Material Safety Data Sheet Printed February 17, 1987 (Dow Chemical U.S.A.) |
| IRA-35 (XE-275) | Acrylic | Amberlite Ion Exchange Resins (XE-275) Rohm & Haas Co. 1975 |
| IRA-68 | Acrylic | Amberlite Ion Exchange Resins-Amberlite IRA-68 Rohm & Haas Co. April 1977 |

Applications for Amberlite polymeric adsorbents suggested in the Rohm and Haas Company literature include decolorizing pulp mill bleaching effluent, decolorizing dye wastes and removing pesticides from waste effluent. There is, of course, no hint in the literature of the effectiveness of Amberlite polymeric adsorbents in the separation of an organic acid from fermentation broths.

A second class of adsorbents to be used in the process of this invention will comprise strongly basic anion exchange resins possessing quaternary ammonium functionality in a cross-linked polymeric matrix, e.g., divinylbenzene cross-linked acrylic or styrene resins. It is also necessary that these be in the sulfate form, as described below. They have a high degree of uniform polymeric porosity and exhibit chemical and physical stability and are especially suitable when produced in bead form.

Looking at the quaternary ammonium function-containing strongly basic anionic exchange resins of the invention, the quaternary ammonium ion has a positive charge and can form an ionic bond with the sulfate ion. The sulfate form of quaternary ammonium anion exchange resin has a weakly basic property, which, in turn, can adsorb an organic acid through an acid-base interaction.

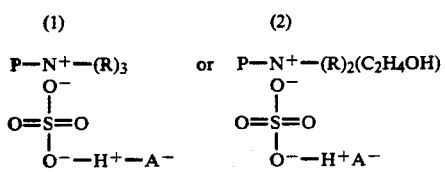

where
P = resinous moiety
R = lower alkyl, $C_{1-3}$
A = Organic acid anion

Adsorbents such as just described are manufactured by the Rohm and Haas Company, and sold under the trade name "Amberlite". The types of Amberlite polymers known to be effective for use by this invention are referred to in Rohm and Haas Company literature as Amberlite IRA 400 and 900 series adsorbents described in the literature as "insoluble in all common solvents, open structure for effective adsorption and desorption of large molecules without loss of capacity, due to organic fouling." Also suitable are AG1, AG2 and AGMP-1 resins manufactured by Bio Rad and comparable resins sold by Dow Chemical Co., such as Dowex 1, 2, 11, MSA-1 and MSA-2, etc. Also useful in this invention are the so-called intermediate base ion exchange which are mixtures of strong and weak base exchange resins. Among these are the following commercially available resins: Bio-Rex 5 (Bio-Rad 1); Amberlite IRA-47 and Duolite A-340 (both Rohm & Haas). For example, they may be useful where a basic ion exchange resin is needed which is not as basic as the strong base resins, or one which is more basic than the weakly basic resins.

Various strongly basic anionic exchange resins are available and will also differ in physical properties such as porosity (volume percent), skeletal density, nominal mesh sizes, surface area, average pore diameter and dipole moment. The preferred adsorbents will have surface area of 10–2000 square meters per gram and preferably from 100–1000 $m^2/g$. Specific properties of the materials listed above can be found in company literature and technical brochures, such as those mentioned in the following Table 2 which are incorporated herein by reference.

TABLE 2

| STRONGLY BASIC ANIONIC EXCHANGE RESINS | | |
|---|---|---|
| Adsorbent | Matrix Resin Type | Reference to Company Literature |
| IRA 458 (Rohm & Haas) | Acrylic gel-type | Amberlite Ion Exchange Resins 1986 & Technical Bulletin IE-207-74 84 |
| IRA 958 | Acrylic macroporous | Technical Bulletin and Material Safety Data Sheet are available |
| IRA 900 | Polystyrene macroporous | Technical Bulletin is available and Amberlite Ion Exchange Resins, IE-100-66. |
| IRA 904 | Polystyrene macroporous | Technical Bulletin, 1979 and IE-208/74, Jan. 1974 |
| IRA 910 | Polystyrene macroporous | Technical Bulletin, 1979 and IE-101-66, May 1972 |
| IRA 400, 402 | Polystyrene macroporous | Amberlite Ion Exchange Resins, Oct., Sept. 1976, April 1972 and IE-69-62, October 1976 |
| IRA 410 | Polystyrene gel-type | Amberlite Ion Exchange Resins IE-72-63, August 1970 |
| AG 1 (Bio Rad) | Polystyrene gel-type | Chromatography Electrophoresis Immunochemistry Molecular Biology HPLC, Price List M April 1987 |
| AG 2 | Polystyrene gel-type | Chromatography Electrophoresis Immunochemistry Molecular Biology HPLC, Price List M April 1987 |
| AG-MP-1 | Polystyrene macroporous | Chromatography Electrophoresis Immunochemistry Molecular Biology HPLC, Price List M April 1987 |
| Bio Rex 5 (Bio Rad) | Mixture of strong base and weak base resins (e.g. AG-2 and AG-3 or AG-4 | Chromatography Electrophoresis Immunochemistry Molecular Biology HPLC, Price List M April 1987 |

In the practice of the invention, the adsorbents set forth above are in the sulfate form. Therefore, the commercial adsorbent listed above must be converted from the form as received, in most cases the chloride or the free base, to the sulfate, which in itself is known in the art. As applicants practice the conversion, the adsorbent is placed in a column and 1N $H_2SO_4$ is passed through the column at a liquid hourly space velocity (LHSV) of 1 $hr^{-1}$ until the adsorbent has been contacted with a 100% excess of the amount of sulfate ion calculated to convert the entire resin capacity. After washing the adsorbent bed with 5 bed volumes of water, the adsorbent is ready for use.

The adsorbent may be employed in the form of a dense compact fixed bed which is alternatively contacted with the feed mixture and desorbent materials. In the simplest embodiment of the invention the adsorbent is employed in the form of a single static bed in which case the process is only semicontinuous. In another embodiment a set of two or more static beds may be employed in fixed bed contacting with appropriate valving so that the feed mixture is passed through one or more of the other beds in the set. The flow of feed mixture and desorbent materials may be either up or down through the desorbent. Any of the conventional apparatus employed in static bed fluid-solid contacting may be used.

Countercurrent moving bed o simulated moving bed countercurrent flow systems, however, have a much greater separation efficiency than fixed adsorbent bed systems and are therefore preferred. In the moving bed or simulated moving bed processes the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in the above mentioned U.S. Pat. No. 2,985,589.

Although both liquid and vapor phase operations can be used in many adsorptive separation processes, liquid-phase operation is preferred for this process because of the lower temperature requirements and because of the higher yields of extract product than can be obtained with liquid-phase operation over those obtained with vapor-phase operation. Adsorption conditions will include a temperature range of from about 20° C. to about 200° C. with about 65° C. to about 100° C. being more preferred, a pressure to ensure liquid phase, e.g. in the range of from about atmospheric to about 500 psig (3450 kPa gauge) with 50 to 100 being more preferred and a pH below the ionization constant (pKa) of the organic acid. Desorption conditions will include the same range of temperatures and pressures as used for adsorption conditions.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber comprising a helical column of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect qualitatively or determine quantitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent, is injected for a duration of several minutes. Desorbent flow is resumed, and the tracer and the extract component or the raffinate component (or both) are eluted as in a liquid-solid chromatographic operation. The effluent can be analyzed on stream or, alternatively, effluent samples can be collected periodically and later analyzed separately by analytical equipment and traces of the envelopes of corresponding component peaks developed.

From information derived from the test adsorbent, performance can be stated in terms of void volume, net retention volume for an extract or a raffinate component, selectivity for one component with respect to the other, the rate of desorption of an extract component by the desorbent and resolution. The net retention volume (NRV) of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during the time interval represented by the distance between the peak envelopes. Selectivity, $\beta$, for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent pumped during this time interval. Resolution is defined earlier.

The following examples are presented to illustrate the relationships that make the process of my invention possible. The examples are not intended to unduly restrict the scope of claims attached hereto.

EXAMPLE I

In this example four pulse tests were run with a weakly basic anion exchange resin having a tertiary amine function hydrogen bonded to a sulfate ion converted from the free base form to the sulfate form in the manner above, in a cross-linked gel-type acrylic resin matrix (AG4-X4 made by Bio Rad Laboratories, Richmond, Cal.) having a tertiary amine function hydrogen bonded to a sulfate ion, in a cross-linked acrylic resin matrix to determine the ability of the adsorbent to separate citric acid from its fermentation mixture of carbohydrates (DP1, DP2, DP3, including glucose, xylose, arabinose and raffinose) and ions of salts, including $Na^+$, $K^+$, $Mg^{++}Ca^{++}$, $Fe^{+++}$, $Cl^-$, $SO_4^=$, $PO_4^=$ and $NO_3^-$, amino acids and proteins at a pH of 1.6. The first test was run at a temperature of 75° C. The remaining tests were run at 60° C. Citric acid was desorbed with water in Pulse Test No. 1 and sulfuric acid in two concentrations: 0.05N (Pulse Test No. 2) and 0.25N (Pulse Test No. 3). Pulse Test No. 4 was like Pulse Test No. 2 except that it was made after the adsorbent was used with 24 bed volumes of feed. The fermentation feed mixture had the following composition:

| Feed Composition | Wt. % (Dry Basis) |
|---|---|
| Citric Acid | 40% |
| Salts ($K^+$, $Na^+$, $Ca^{++}$, $Mg^{++}$ $Fe^{+++}$) | 1.5% |
| Carbohydrates (Sugars) | 4% |
| Others ($SO_4^=$, $Cl^-PO_4^=$, $NO_3^-$, proteins and amino acids) | 5% |
| Water | 49.5% |

Retention volumes and separation factor ($\beta$) were obtained using the pulse test apparatus and procedure previously described in Example I except that a 5 cc sample was used. The net retention volume (NRV) for the citric acid was calculated by measuring the distance from the midpoint of the salt envelope as the reference point to the midpoint of the citric acid envelope. The separation factor, $\beta$, is calculated from the ratio of the retention volumes of the components to be separated to the retention volume for the first salt component (i.e., Salts 1).

The results for these pulse tests are shown in the following Table No. 3. The results of Pulse Test No. 1 are also shown in FIG. 2.

TABLE NO. 3

| Pulse Test | Resin/Desorbent | Feed Component | NRV | β |
|---|---|---|---|---|
| 1 | AG4-X4/Water | Salts 1 | 1.6 | 34.25 |
| | | Citric Acid | 54.8 | Reference |
| | | Unknowns A | 0 | Tracer |
| | | Unknowns B | 6.6 | 8.30 |
| | | Salts 2 | 54.6 | 1.00 |
| 2 | AG4-X4/0.05 N H₂SO₄ | Salts | 3.2 | 11.87 |
| | | Citric Acid | 38.0 | Reference |
| | | Unknown A | 0 | Tracer |
| | | Unknown B | 2.7 | 14.07 |
| 3 | AG4-X4/0.25 N H₂SO₄ | Unknowns A | 0 | Tracer |
| | | Citric Acid | 26.9 | Reference |
| | | Salts | 2.3 | 11.70 |
| | | Unknowns B | 7.6 | 3.54 |
| 4 | AG4-X4/0.05 N H₂SO₄ | Unknowns A | 0 | Tracer |
| | | Citric Acid | 38.0 | Reference |
| | | Salts | 2.4 | 15.8 |
| | | Unknowns B | 7.2 | 5.28 |

Figure 2:
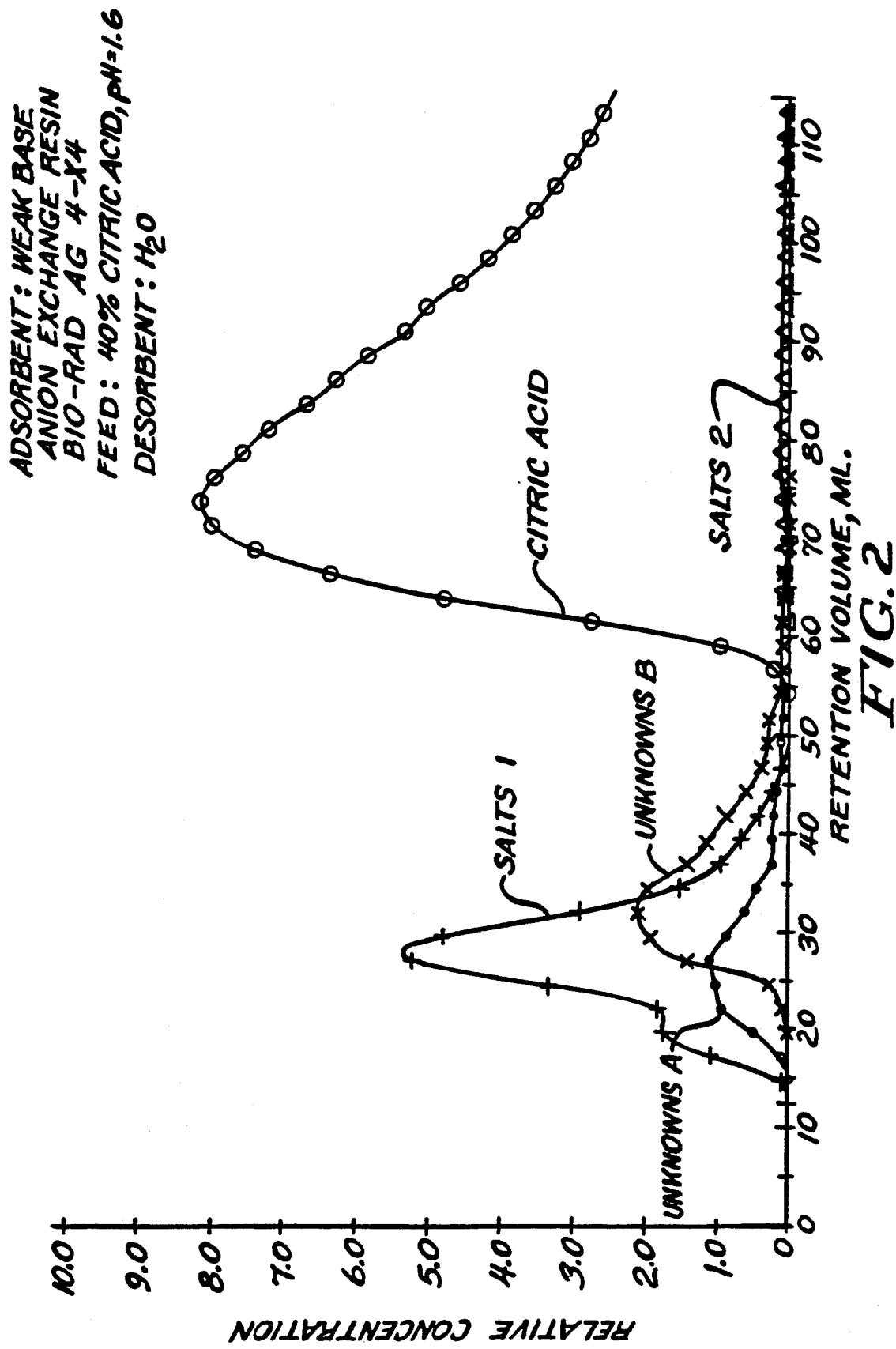
FIG. 2 is the plot of the pulse test in Example I using a weakly basic anionic exchange resin having a tertiary amine functionality in a cross-linked acrylic resin matrix to separate citric acid from a feed containing 40% citric acid at a pH of 1.6, desorbed with water.

The results of Pulse Tests 2-4 are similar to FIG. 2. From Table 3, it is clear that while citric acid is satisfactorily separated in the process, in highly purified form, with water, desorption with water is slower than with dilute sulfuric acid as evidenced by larger net retention volume. After aging the adsorbent with 24 bed volumes of feed, the adsorbent showed no signs of deactivation; the Pulse Test was substantially identical to one conducted under identical conditions with fresh adsorbent.

EXAMPLE II

The first pulse test of Example I was repeated using the same procedure and apparatus except that the temperature was 65° C. The desorbent was water. This example presents the results of using a macroporous weakly basic anionic exchange resin possessing a cross-linked polystyrene matrix (Dowex 66) with the same separation feed mixture as Example I (40% citric acid) in the first two pulse tests at a pH of 7.0 and 3.5 (FIGS. 3 and 4, respectively) to demonstrate the failure to accomplish the desired separation when the pH is above the first ionization constant, $pKa_1 = 3.13$, of citric acid, and more specifically in these two samples, where the concentration of citric acid is 40%, when the pH is above 1.7. In the third part of the example (represented by FIG. 5, the feed was diluted to 13% citric acid and the pH reduced to 2.4. While there is evident improvement, it is apparent that the pH and/or concentration will have to be reduced further to prevent "breakout" of the citric acid. For example, at 13% concentration, it is estimated that the pH must be lowered to about 1.6 to 2.2.

Figure 3:
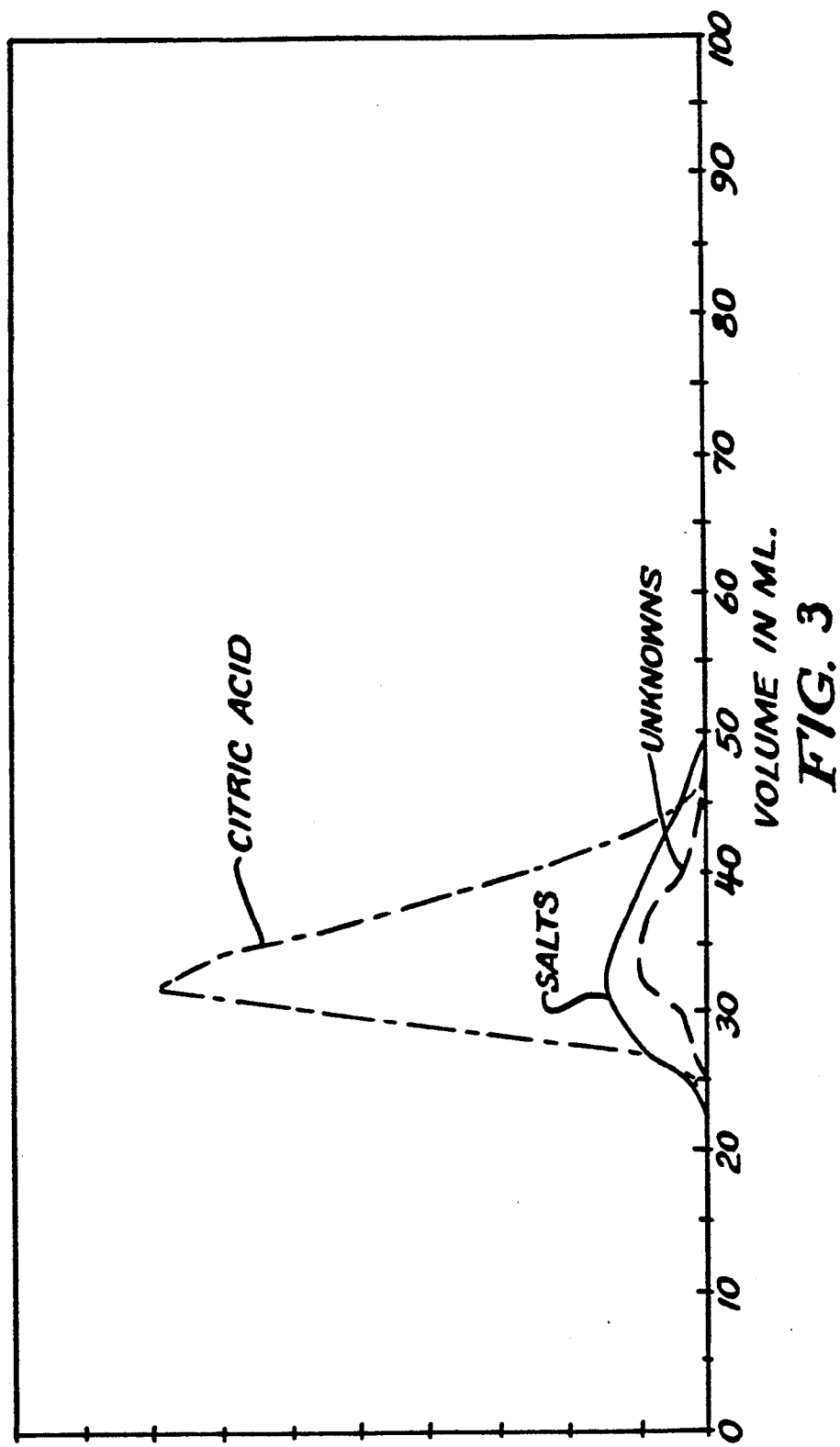
FIGS. 3, 4 and 5 are plots of the pulse tests of Example II at pH's of 7.0, 3.5 and 2.4, respectively.
Figure 4:
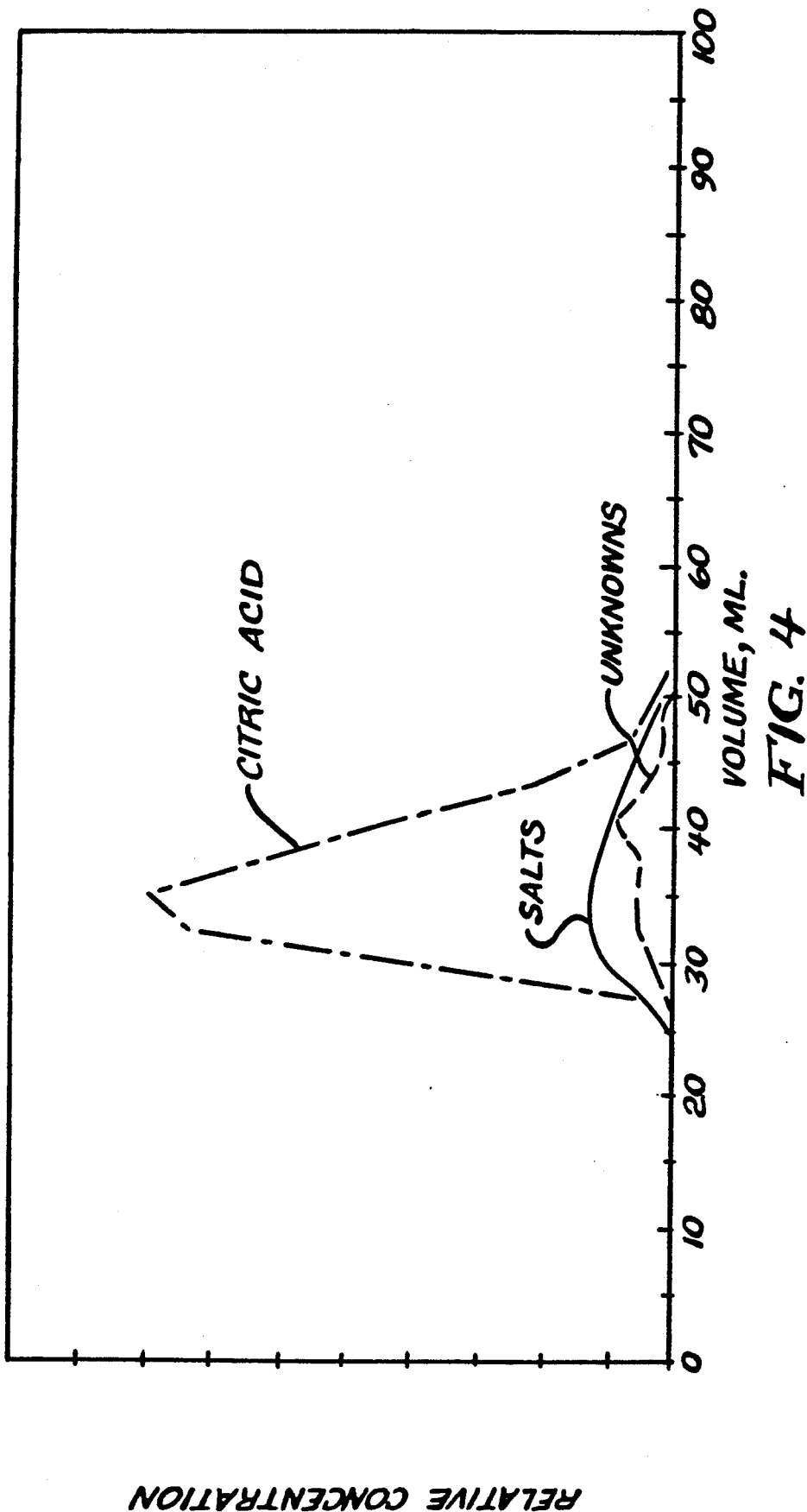
Figure 5:
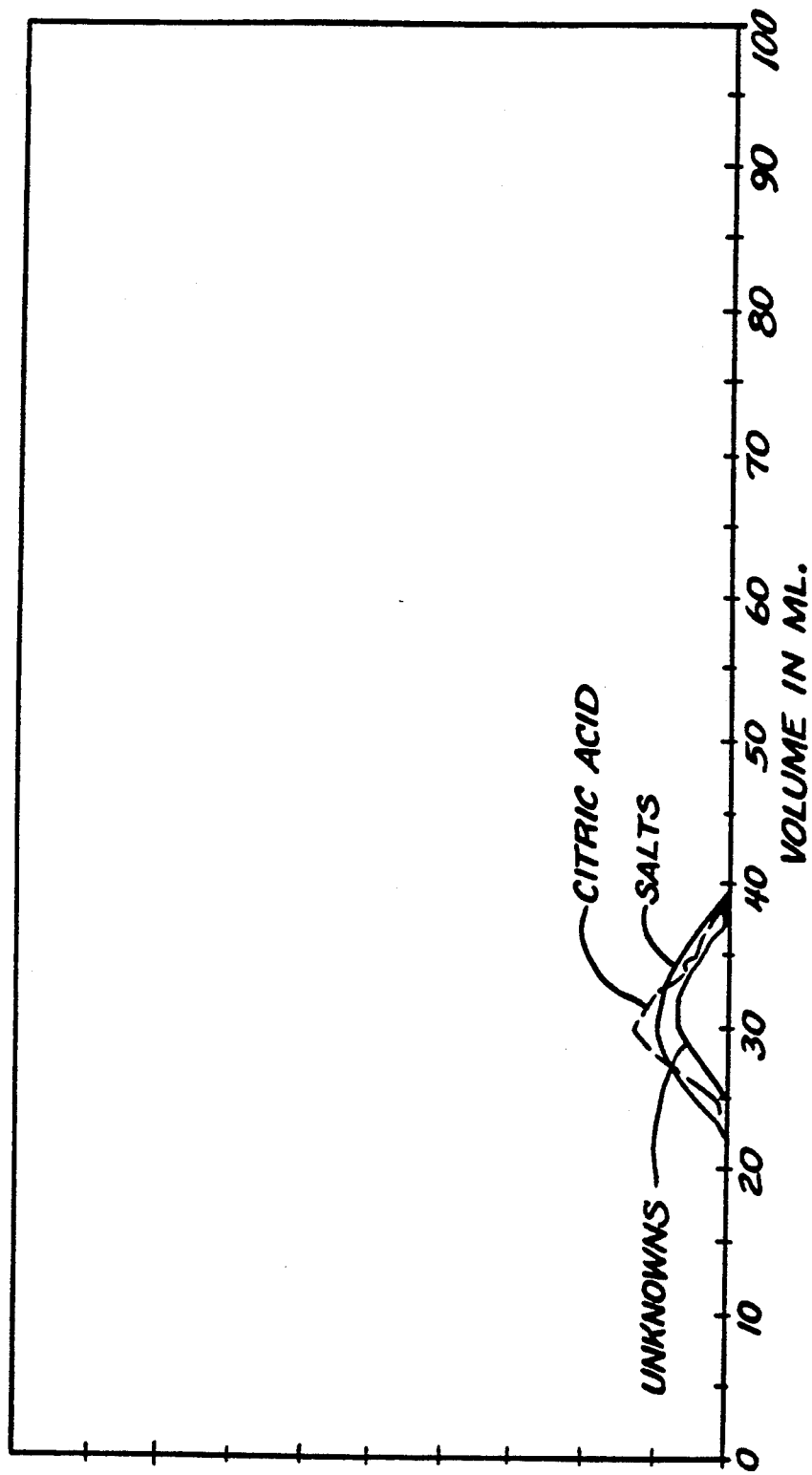

FIGS. 3 and 4 are, respectively, graphical presentation of the results of the pulse test using Dowex 66 at pHs, respectively, of 7.0 and 3.5. FIGS. 3 and 4 show that citric acid "breaks through" with the salts (and carbohydrates) at the higher pHs. This problem can be partially alleviated by reducing the concentration to 13% and lowering the pH to 2.4 as in FIG. 5, where it is shown that only a small amount of citric acid is not adsorbed and "breaks through" in the raffinate while most is adsorbed onto the adsorbent resin (but not desorbed in this Figure). This separation, with adjustment of the concentration and pH to optimum levels, clearly will have commercial utility.

EXAMPLE III

Figure 6:
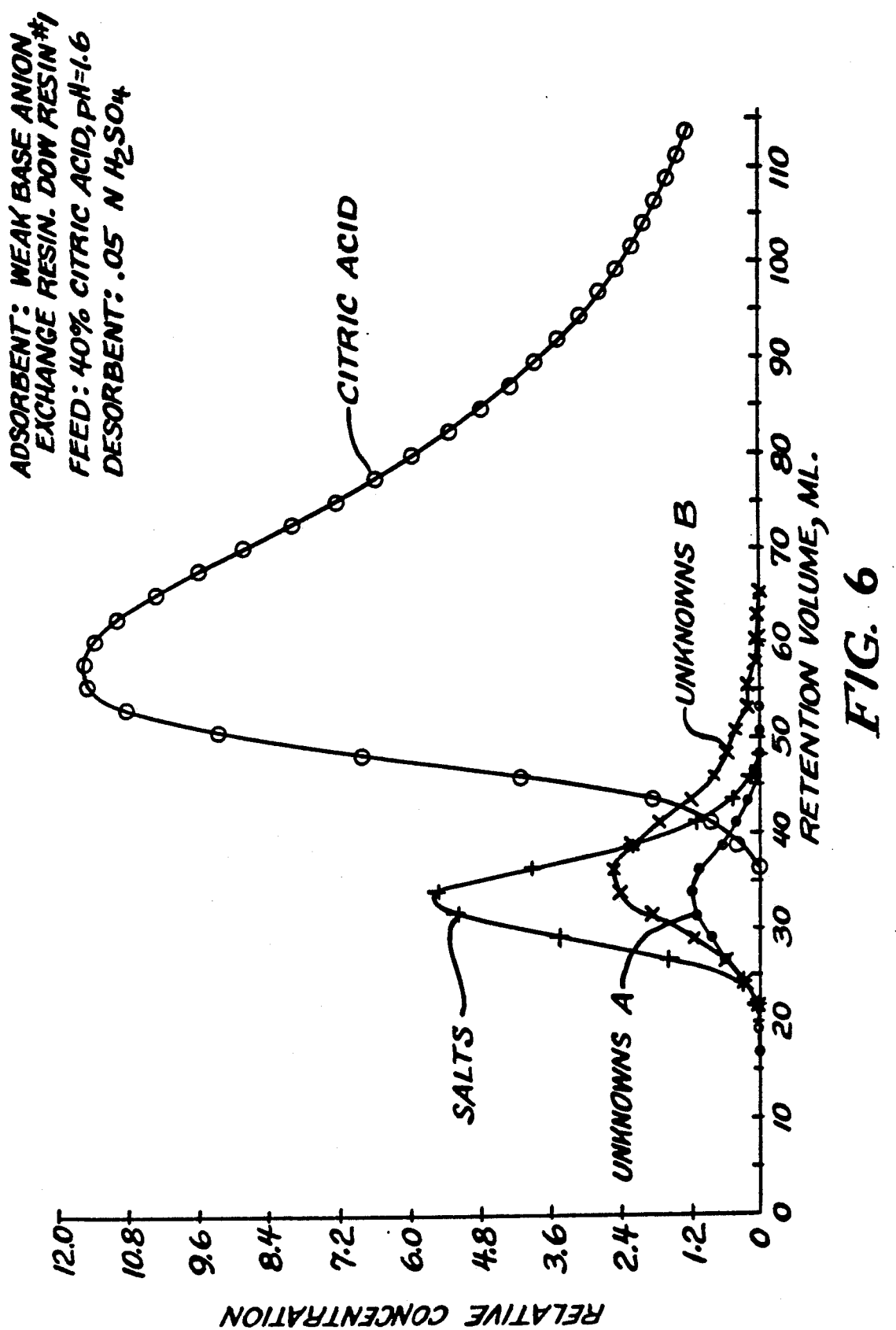
FIGS. 6, 7, and 8 are the plots of the pulse test of Example III at a pH of 1.6 run on several different adsorbent samples of weakly basic anionic exchange resin possessing pyridine functionality in a cross-linked polystyrene resin matrix. The citric acid is desorbed with 0.5N sulfuric acid or water.
Figure 7:
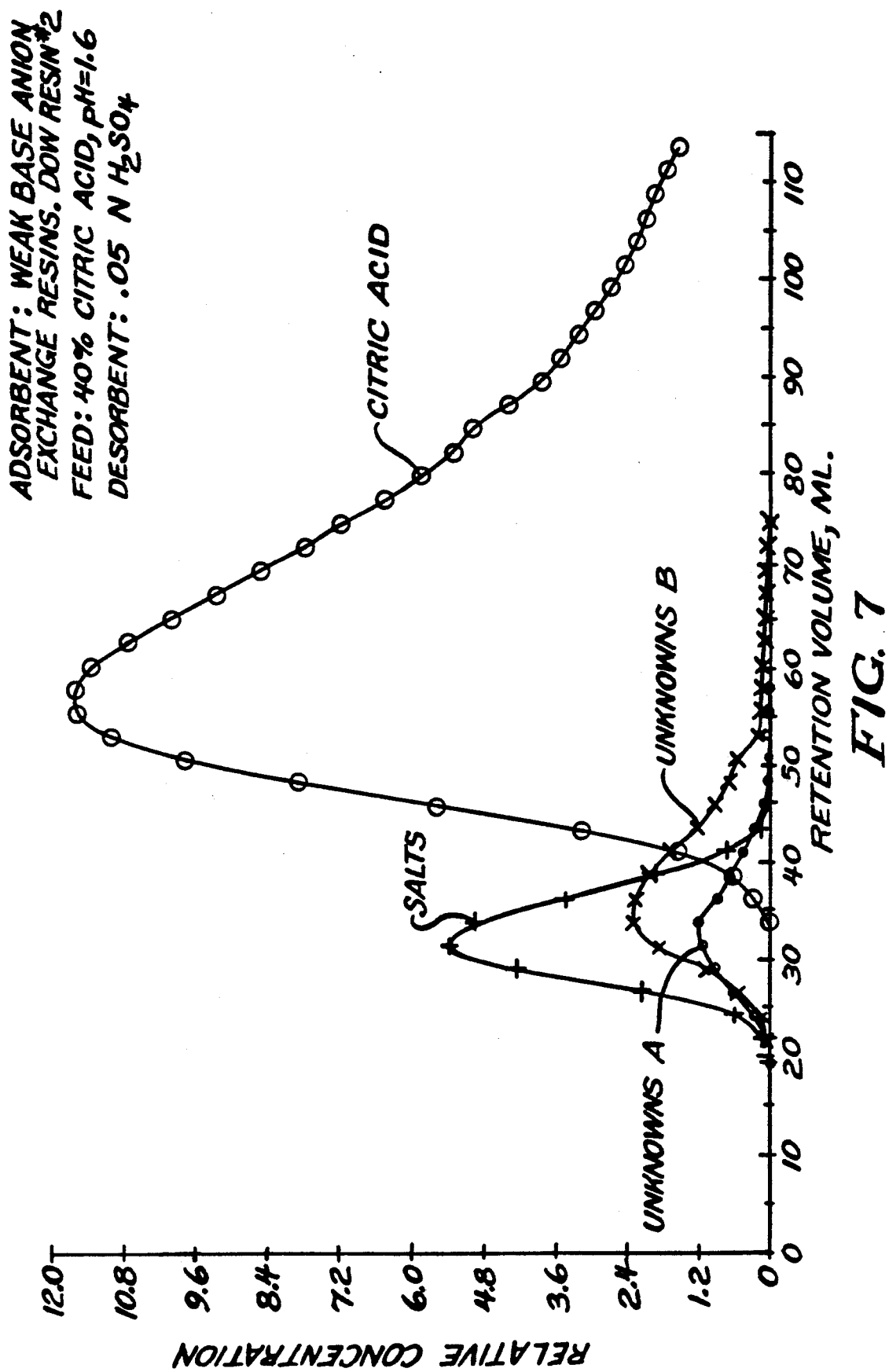
Figure 8:
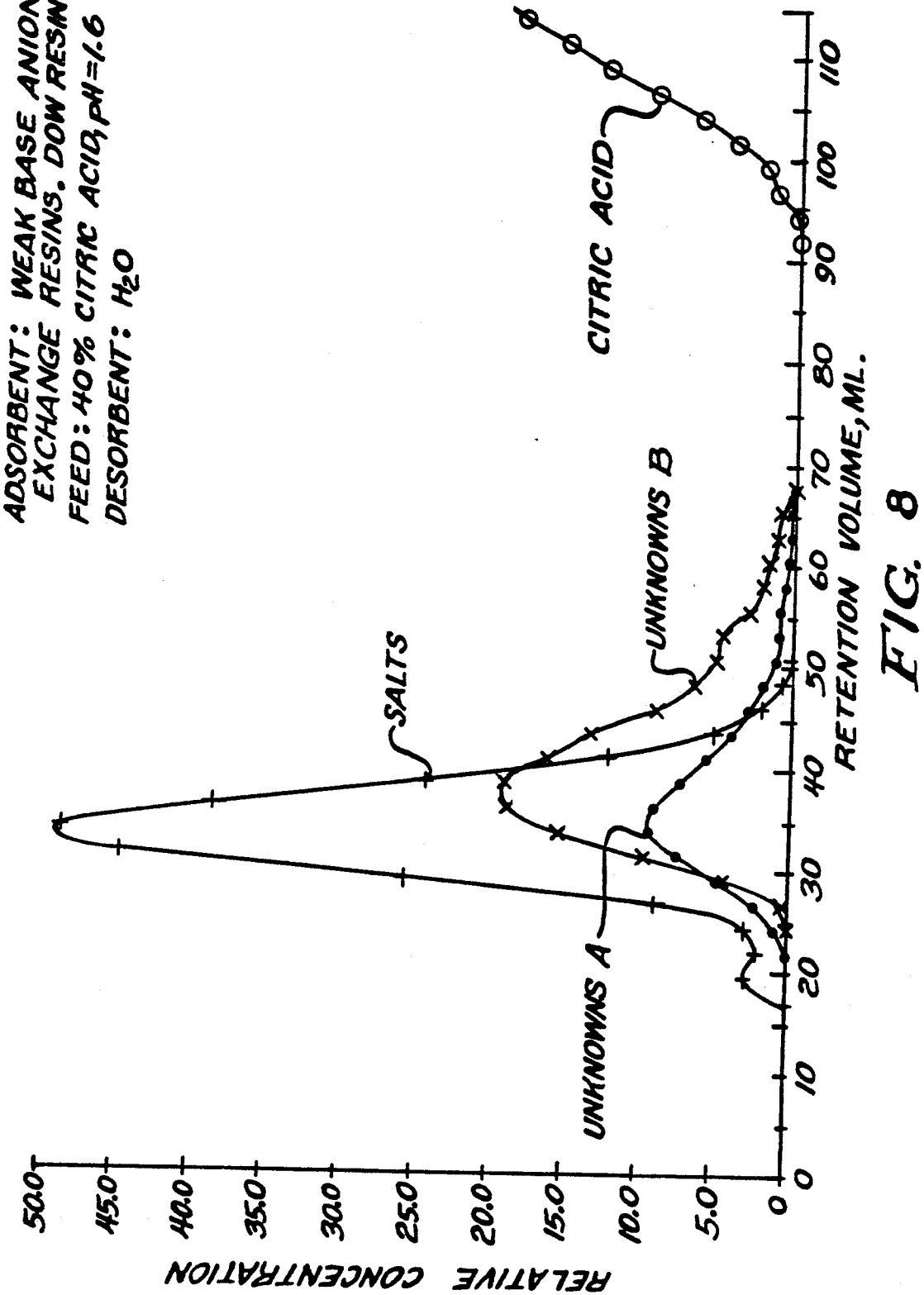

Three additional pulse tests under the same conditions as Example I, except as noted, were made on citric acid samples of the same feed composition, but with two different adsorbents. The desorbent in the first two samples was 0.05N H₂SO₄ (FIGS. 6 and 7) while water was used in the third sample (FIG. 8). The composition of the feed used was the same as used in Example I. The temperature was 60° C. and the pH was 1.6. The adsorbent (Dow Experimental Resin #1) in the first test was a macroporous pyridine function-containing divinylbenzene cross-linked resin of the following formula:

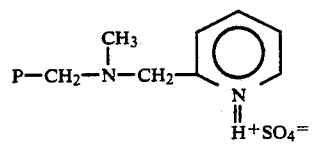

where P is the polystyrene moiety forming the resin. The second adsorbent (Dow Experimental Resin #2), used in the second and third samples, is a tertiary amine, also with a pyridine functional group, having the following formula:

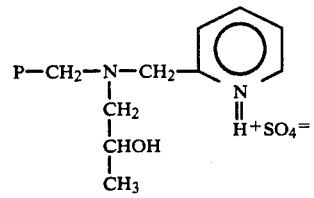

where P is as defined above. Both resins are cross-linked with divinylbenzene. In some cases, while water is an effective desorbent, with excellent separation, it is not strong enough to recover the adsorbed citric acid quickly enough to make the process commercially attractive. See FIG. 8, in which the conditions are the same as above, using adsorbent #2, where water is the desorbent. In this case, citric acid does not elute until about 95 ml of desorbent have passed through the adsorbent. Dilute sulfuric acid is, therefore, the preferred desorbent, as will be apparent from the results shown in FIGS. 6 and 7. Also, from FIGS. 6, 7 and 8, it will be seen that an excellent separation of citric acid is obtained.

EXAMPLE IV

The procedure, conditions and apparatus previously described in Example I were used to separate four samples of citric acid from the same feed with two different resins of the same class of adsorbent as Example I (except that in the first and fourth samples, the column temperature was 50° C. and the desorbent was 0.05N H₂SO₄; in the second and third samples the pH was 2.2 and the desorbent was dilute sulfuric acid at 0.15N concentration). Both resins, IRA-68 and IRA-35, obtained from Rohm and Haas, have an amine function and the following structural formula:

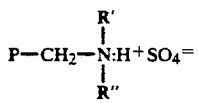

where P is the polyacrylic matrix, and

R' and R"=CH$_3$

Amberlite IRA-68 (Sample Nos. 1, 2, and 3) is a gel-type resin. IRA-35 (Sample No. 4) is a macroreticular type resin. Sample No. 3 was identical to Sample No. 2, except that the adsorbent had previously been used to separate 69 bed volumes of the feed. Samples Nos. 1 and 2 are both excellent adsorbents for separating citric acid from its fermentation broth within the pH range of 1.6 to 2.2. Sample No. 3, after aging the adsorbent with 69 bed volumes of feed, demonstrates the stability of the resin (little or no deactivation has taken place) in this separation. Net retention volume (NRV) and selectivity β are shown in the following Table 4.

TABLE 4

| Sample No. | Resin | Component | NRV | β |
|---|---|---|---|---|
| 1 | Amberlite IRA-68 | Salts | 5.5 | 8.24 |
| | | Citric Acid | 45.3 | Reference |
| | | Unknown A | 0 | Tracer |
| | | Unknown B | 9.3 | 4.87 |
| 2 | Amberlite IRA-68 | Salts | 2.3 | 12.61 |
| | | Citric Acid | 29.0 | Reference |
| | | Unknown A | 0 | Tracer |
| | | Unknown B | 6.5 | 4.46 |
| 3 | Amberlite IRA-68 | Salts | 2.85 | 10.32 |
| | | Citric Acid | 29.4 | Reference |
| | | Unknown A | 0 | Tracer |
| | | Unknown B | 7.0 | 4.2 |
| 4 | Amberlite IRA-35 | Salts | 1.3 | 27.38 |
| | | Citric Acid | 36.9 | Reference |
| | | Unknown A | 0 | Tracer |
| | | Unknown B | 5.9 | 6.25 |

In a further comparison of the adsorbents of U.S. Pat. No. 4,720,579 with Examples I through IV of this application, several samples of the extract were analyzed for readily carbonizable impurities (RCS) (Food & Chemical Codex (FCC) Monograph #3) and potassium level. RCS is determined in the following manner: a 1 gm sample of the extract (actual concentration of citric acid is determined) is carbonized at 90° C. with 10 ml of 95% H$_2$SO$_4$. The carbonized substance is spectrophotometrically measured at 500 nm using a 2-cm cell with an 0.5 inch diameter tube and the amount of RCS is calculated for 50% citric acid solution. The number arrived at can be compared with that obtained by using this procedure on the cobalt standard solution of the FCC test mentioned above. Potassium is determined by atomic adsorption spectroscopy. For comparison, the same analytical determinations were made on a sample of the same feed and RCS calculated for citric acid with XAD-4, a neutral resin disclosed in said U.S. Pat. No. 4,720,579, and with AG4-X4, and adsorbents No. 1 and No. 2 of Example III herein. The results are shown in Table 5.

TABLE 5

EXTRACT QUALITY (RCS/POTASSIUM) BY PULSE TEST

| Adsorbent | Desorbent | RCS Calculated (for 50% C.A.) | ppmK | C.A. Net Ret. Vol. |
|---|---|---|---|---|
| XAD-4 | H$_2$O | 6.86, 8.98 | 59, 137 | 13.0 |
| (4,720,579) AG4-X4 | .05 N.H$_2$SO$_4$ | 1.77, 1.42 | 24, 81 | 34.8 |
| #2 (Ex.III) | .05 N.H$_2$SO$_4$ | 3.17, 3.33 | 24, 54 | 30.8 |
| #1 (Ex.III) | .05 N.H$_2$SO$_4$ | 2.17 | 62 | 31.0 |

An improvement in both reduction levels of RCS and K for the weakly basic resins compared to the neutral resins of U.S. Pat. No. 4,720,579 is indicated by this data. In all samples, RCS was reduced by at least 50% and in two samples, K was reduced by over 50%. It is noted from the net retention volume that both classes of adsorbents have good resolution, but the strong base adsorbents suffer somewhat from increased cycle times. The cycle times can be reduced by using higher concentrations of sulfuric acid, e.g., up to about 0.2N, in the preferred range of 0.1 to 0.2N.

In another embodiment, citric acid adsorbed on the adsorbent may be converted in situ to a citrate before being desorbed, for example, by reaction with an alkaline earth metal or alkali metal hydroxide or ammonium hydroxide and then immediately eluted using a metal hydroxide; ammonium hydroxide or water as the desorbent. Deactivation of the adsorbent by the unknown impurities may take place in time, but the adsorbent may be regenerated by flushing with a stronger desorbent, e.g., a higher concentration of sulfuric acid than the desorbent, an alkali metal hydroxide or NH$_4$OH, or an organic solvent, e.g., acetone or alcohol.

EXAMPLE V

In this example, two pulse tests were run with a gel-type strongly basic anion exchange resin (IRA 458 made by Rohm & Haas Co.) having the structural formula like (1) on page 24 above, substituted with three methyl groups, to determine the ability of the adsorbent to separate citric acid from its fermentation mixture of carbohydrates (DP1, DP2, DP3, including glucose, xylose, arabinose and raffinose) and ions of salts, including Na$^+$, K$^+$, Mg$^{++}$, Ca$^{++}$, Fe$^{+++}$, Cl$^-$, SO$_4^=$, PO$_4^\equiv$ and NO$_3^-$, amino acids and proteins at a pH of 2.2. The matrix is an acrylic resin crosslinked with divinylbenzene. Pulse test Sample No. 1 was run at a temperature of 50° C. Pulse test Sample No. 2 was run at 60° C., but after the bed had been aged with 33 bed volumes of feed. Further runs to 62 bed volumes have been made with no signs of deactivation of the adsorbent. Citric acid was desorbed with 0.1N solution of sulfuric acid in both samples. The fermentation feed mixture had the following composition:

| Feed Composition | Percent |
|---|---|
| Citric Acid | 40 |
| Salts (K$^+$, Na$^+$, Ca$^{++}$, Mg$^{++}$, Fe$^{+++}$) | 1.5 |
| Carbohydrates (Sugars) | 4 |
| Others (SO$_4^=$, Cl$^-$, PO$_4^=$ NO$_3^-$, proteins and amino acids) | 5 |
| Water | 49.5 |

Retention volumes and separation factor were obtained using the pulse test apparatus and procedure previously described in Example I.

The results for these pulse tests are shown in the following Table No. 6.

TABLE NO. 6

| Sample No. | Resin | Feed Component | NRV | β |
|---|---|---|---|---|
| 1 | IRA-458 | Salts | 1.0 | 38.9 |
| | | Citric Acid | 38.9 | Reference |
| | | Unknowns A | 0 | Tracer |
| | | Unknowns B | 6.6 | 5.89 |
| 2 | IRA-458 | Salts | 0.9 | 43.3 |
| | | Citric Acid | 39.0 | Reference |
| | | Unknown A | 0 | Tracer |
| | | Unknown B | 7.1 | 5.49 |

It is clear that citric acid is satisfactorily separated in the process, and after aging the adsorbent with 33 bed volumes of feed, the adsorbent shows no signs of deactivation, which is substantially identical to the results under closely identical conditions with fresh adsorbent.

EXAMPLE VI

The pulse test of Example V was repeated on additional citric acid samples using the same feed, but a different, macroporous, strongly basic anionic exchange adsorbents, IRA-958, possessing quaternary ammonium functions and an acrylic resin matrix cross-linked with divinylbenzene matrix. The desorbent was 0.05N $H_2SO_4$. The composition of the feed used was the same as used in Example V. The temperature was 60° C. and the pH was 1.6. The adsorbent in this test was a resin obtained from Rohm & Haas having the structure (1) shown on page 24, where R is methyl.

Figure 9:
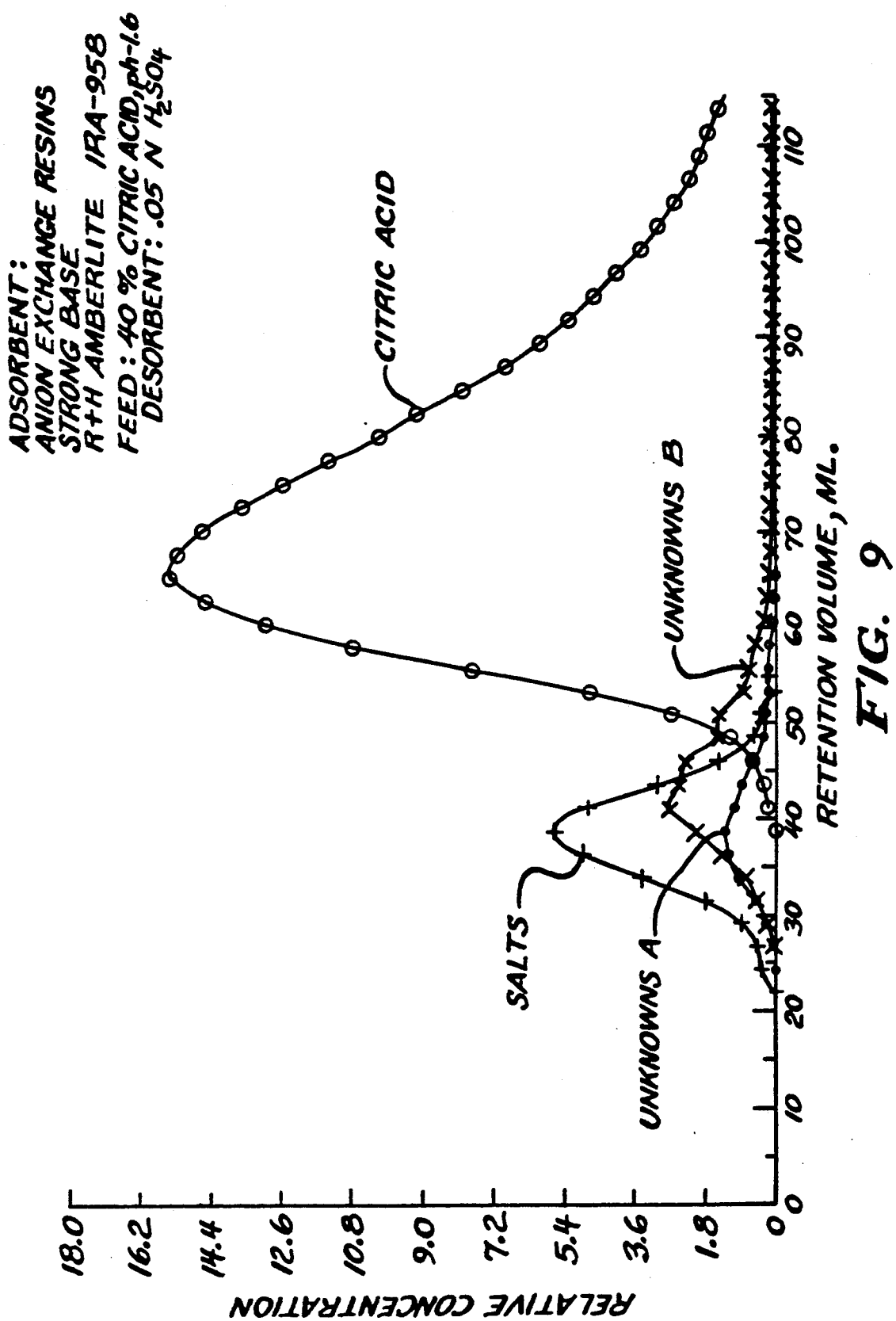
FIG. 9 is a plot of the pulse test of Example VI at a pH of 1.6.

As shown in FIG. 9, citric acid starts eluting after 45 ml of desorbent have passed through the adsorbent and is very effectively separated from the fermentation mixture in high purity with excellent recovery.

EXAMPLE VII

The pulse test of Example V was repeated on an additional citric acid sample using the same feed, but a different, strongly basic anionic exchange resin adsorbent, AG2-X8 (obtained from Bio Rad Company) having a structure like formula (2) above, (page 24) where R is methyl, with a cross-linked polystyrene gel-type resin matrix having quaternary ammonium functional groups thereon. The desorbent was 0.15N $H_2SO_4$. The composition of the feed used was the same as used in Example IV. The temperature was 50° C. and the pH was 2.2.

Figure 10:
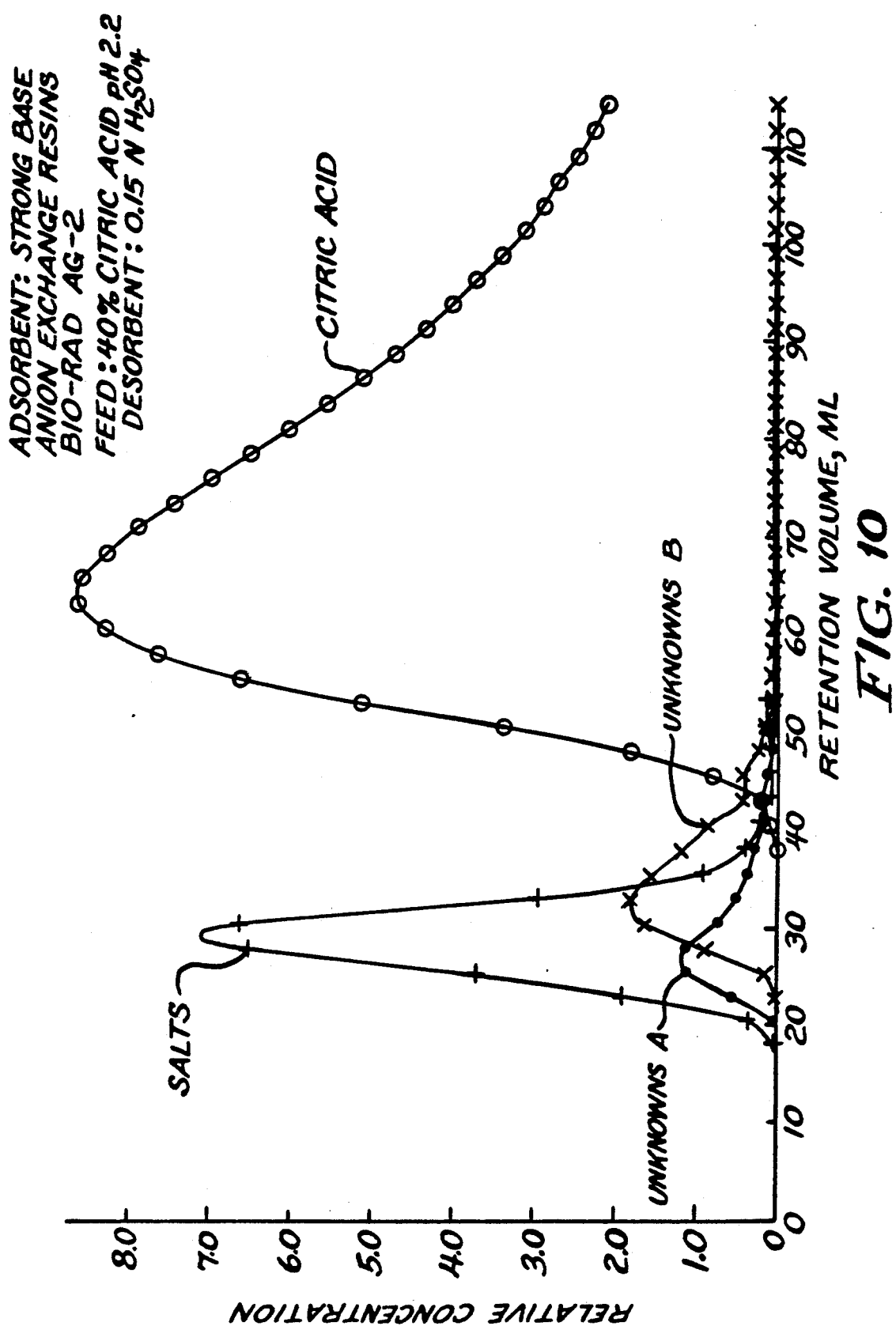
FIG. 10 is the plot of the pulse test of Example VII at a pH of 2.2 run on a different adsorbent sample of a less strongly basic anionic exchange resin possessing quaternary ammonium functionality in a cross-linked polystyrene resin matrix, desorbed with dilute sulfuric acid.

As shown in FIG. 10, citric acid starts eluting after about 43 ml of desorbent have passed through the adsorbent and is very effectively separated from the fermentation mixture in high purity with excellent recovery.

In a further comparison of adsorbents of U.S. Pat. No. 4,720,579 and Examples V through VII of this application, several samples of the extract were analyzed for readily carbonizable impurities (RCS) (Food & Chemical Codex (FCC) Monograph #3) and potassium level as described above. The results for each of the adsorbents, XAD-4, IRA 458, IRA 959 and AG2-X4 with the indicated desorbent are shown in the following Table 7.

TABLE 7

| Adsorbent | Desorbent | RCS (Calculated at 50% CA) (Units) | ppmK (Calculated at 50% C.A.) | CA Net Retention Volume |
|---|---|---|---|---|
| XAD-4 (4,720,579) | $H_2O$ | 6.86 / 8.98 | 59 / 137 | 13.0 |
| IRA 458 (Ex. V) | 0.1 N $H_2SO_4$ | 1.5 | 80 | 37.9 |
| IRA 958 (Ex. VI) | 0.05 N $H_2SO_4$ | 2.73 | 82 | 32 |
| AG2-X4 (Ex. VII) | 0.15 N $H_2SO_4$ | 5.3 | 131 | 43 |

An improvement in both reduction of levels of RCS and K for the strongly basic resins compared to the neutral resins of U.S. Pat. No. 4,720,579 is indicated by this data. In all samples, RCS was reduced by between 40–85% and K was reduced between 0–20%. It is noted from Example V, Example VI (FIG. 9) and Example VII (FIG. 10) that both classes of adsorbents have good separation, but the present adsorbents suffer somewhat from increased cycle times. The cycle times can be reduced by using higher concentrations of sulfuric acid, e.g., up to about 0.2N in the preferred range of 0.1 to 0.2N.

In another embodiment, citric acid, adsorbed on the adsorbent may be converted in situ to a citrate before being desorbed, for example, by reaction with an alkaline earth metal hydroxide, alkali metal hydroxide or ammonium hydroxide and then immediately eluted using a metal hydroxide, ammonium hydroxide or water, as the desorbent. Deactivation of the adsorbent by the unknown impurities may take place in time, but the adsorbent may be regenerated by flushing with a stronger desorbent, e.g., a high concentration of sulfuric acid than the desorbent, an alkali metal hydroxide or $NH_4OH$, or an organic solvent, e.g., acetone or alcohol.

EXAMPLE VIII

In this example a pulse test was run with a weakly basic anionic exchange resin having a tertiary amine functionality in sulfate form in a divinylbenzene cross-linked acrylic resin matrix to determine the ability of the adsorbent to separate lactic acid from its fermentation mixture of carbohydrates (DP1, DP2, DP3, including dextrose), ions of salts, including $Na^+$, $K^+$, $Mg^{++}$, $Ca^{++}$, $Cl^-$, $SO_4^=$, $PO_4^{\equiv}$ and $NO_3^-$, amino acids and proteins. The test was run at 60° C. The pH of the feed was 2.0. Lactic acid was desorbed with 0.02N sulfuric acid. The fermentation feed mixture had the following composition:

| Feed Composition | Wt. % (Dry Basis) |
|---|---|
| Lactic Acid | 57.14 |
| DP3 and Salts($K^+$, $Na^+$, $Ca^{++}$, $Mg^{++}$, $P^{+++}$) | 32.90 |
| Dextrose, DP2 and Unknowns (B1) | 2.58 |
| Acetic Acid | 1.74 |
| Ethanol | 0.242 |
| Unknowns (A2) | 2.73 |
| Unknowns (A1) | 1.16 |

The adsorbent was Amberlite IRA-35 (Rohm and Haas Company) which was treated with 1N sulfuric acid at an LHSV of 1 $hr^{-1}$ as aforesaid to convert the entire resin capacity to sulfate. In this case, 70 ml of adsorbent was placed in a column, and 350 ml of 1N H₂SO₄ was passed through the column. The adsorbent was then washed with 350 ml of deionized water (5 bed volume) before use.

Retention volumes and resolution were obtained using the pulse test apparatus and procedure previously described. Specifically, the adsorbent was tested in a 70 cc straight column using the following sequence of operations for the pulse test. Desorbent material was continuously run upwardly through the column containing the adsorbent at a flow rate of 1.25 cc/min. (a nominal liquid hourly space velocity (LHSV) of about 1.0 hr$^{-1}$). At a convenient time the flow of desorbent material was stopped, and a 5 cc sample of feed mixture was injected into the column via a sample loop and the flow of desorbent material was resumed. Samples of the effluent were automatically collected in an automatic sample collector and later analyzed for salts and lactic acid by chromatographic analysis. Carbohydrates were not separately analyzed in these examples nor were other minor ingredients, amino acids and proteins. Acetic acid was analyzed with unknowns A2 (probably one of the groups of carbohydrates); dextrose was analyzed with unknowns B1. A third group of unknown components, A1, probably also carbohydrates, was also analyzed with ethanol. From the analysis of these samples, peak envelope concentrations were developed for the feed mixture components. The net retention volume (NRV) for the lactic acid was calculated by measuring the distance from the midpoint of the net retention volume of the salt envelope (as the reference point) to the midpoint of the lactic acid envelope. NRV is calculated as the difference between gross retention volume (GRV) of the component and the void volume (GRV of the tracer or raffinate component, in this case, the salts and DP3). Selectivity, $\beta$, was calculated as previously indicated, as the ratio of the net retention volume (NRV) of the extract product to the NRV of the component. The resolution, R, is calculated from Equation 4, given earlier.

The results for the pulse test are shown in the following Table 8.

TABLE 8

| Component | NRV (ml) | GRV (ml) | β | Width at Half Height (ml) | R |
|---|---|---|---|---|---|
| Salts & DP3 | 0.0 | 45.3 | 0.00 | 15.9 | 0.63 |
| Lactic Acid | 12.8 | 58.1 | ref. | 24.9 | — |
| B1 + Dextrose | 2.9 | 48.2 | 4.41 | 20.3 | 0.44 |
| Unk. A1 + Ethanol | 11.0 | 56.3 | 1.16 | 19.8 | 0.08 |
| A2 + Acetic Acid | 5.3 | 50.6 | 2.41 | 20.4 | 0.33 |

Figure 11:
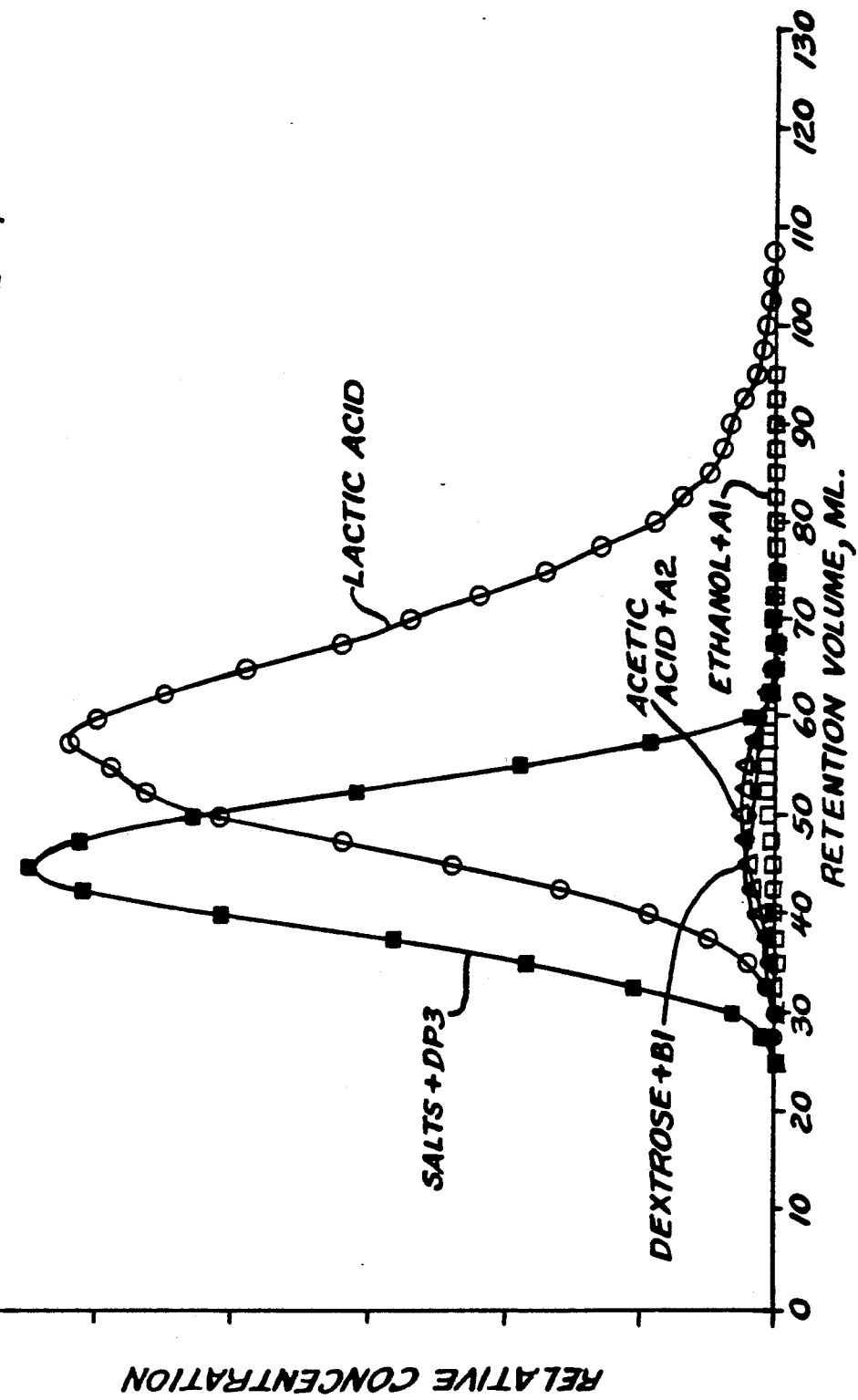
FIG. 11 is the plot of the pulse test in Example VIII using a weakly basic anionic exchange resin in sulfate form in a cross-linked acrylic resin matrix to separate lactic acid from a feed containing lactic acid. Lactic acid is desorbed with dilute sulfuric acid.

The results are also shown in FIG. 11 in which it is clear that lactic acid is more strongly adsorbed than the other components.

EXAMPLE IX

This example presents the results of using a strongly basic anionic resin having quaternary ammonium functionality in sulfate form in a divinylbenzene crosslinked acrylic resin matrix (Amberlite IRA958) to separate the same feed mixture as Example VIII at two different pHs, i.e., below the pKa=3.86 of lactic acid and two concentrations. The same procedure and apparatus as described in the previous examples were used in both the separation and the preparation of the sulfate form of the resin.

Figure 12:
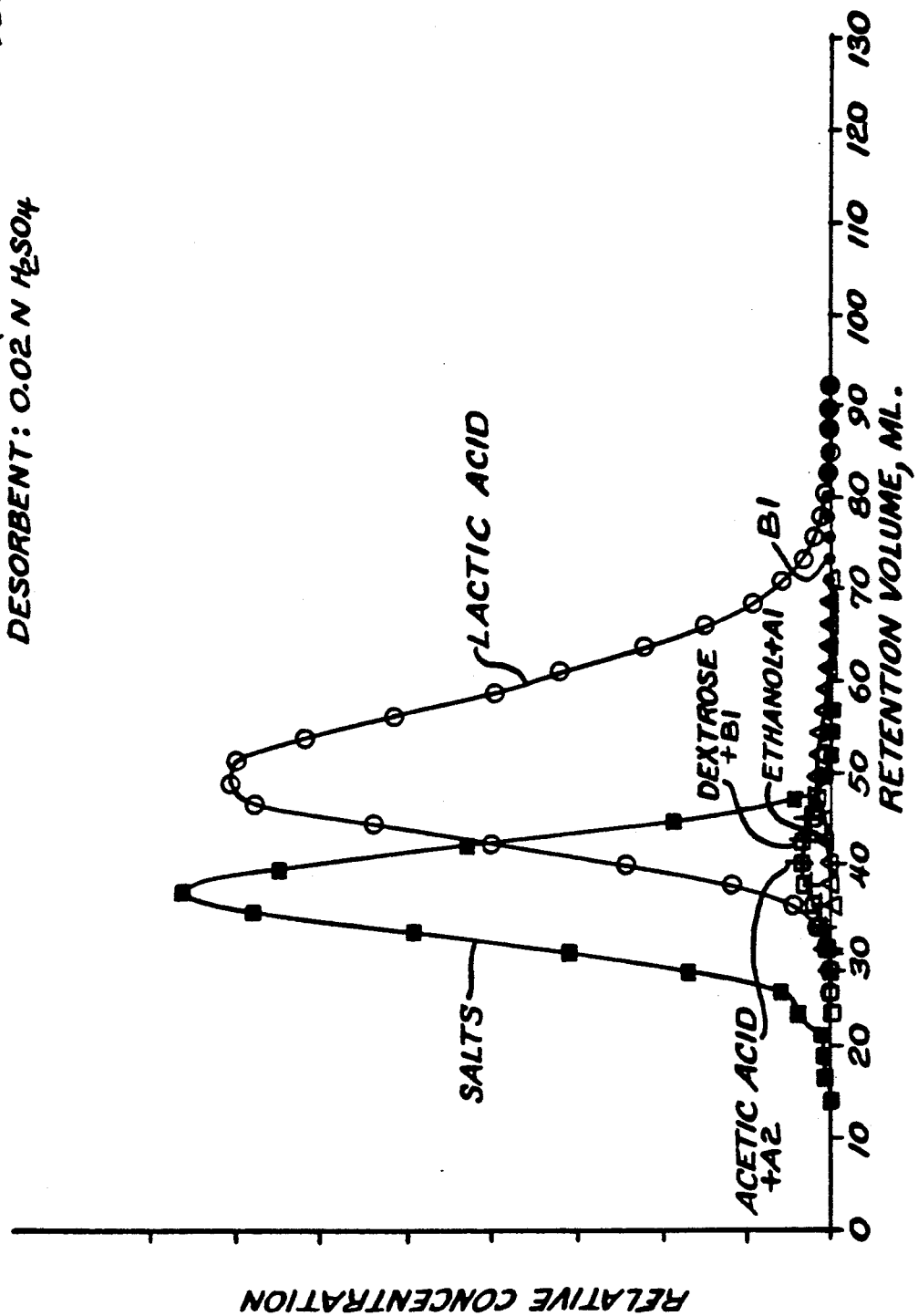
FIG. 12 is the plot of the pulse test of Example IX with a strongly basic anionic exchange resin adsorbent in sulfate form in a cross-linked acrylic resin matrix. The lactic acid is desorbed with dilute sulfuric acid.

FIG. 12 is a graphical presentation of the result of the first pulse test using Amberlite IRA958 at a pH of 2.0 and lactic acid concentration of 9.44% (wet), using 0.02N H₂SO₄ as the desorbent. In the second run, the feed was diluted with water to 30% lactic acid and pH was 1.5. The results of Test No. 1 and 2 are shown in the following Tables 9 and 10, respectively:

TABLE 9

| Component | NRV (ml) | GRV (ml) | β | Width at Half Height (ml) | R |
|---|---|---|---|---|---|
| Salts & DP3 | 0.0 | 37.3 | 0.00 | 11.0 | 0.93 |
| Lactic Acid | 13.8 | 51.0 | ref. | 18.5 | — |
| Unk. B1 | 38.2 | 75.5 | 0.36 | 18.9 | 1.31 |
| Unk. B2 + Dextrose | 3.3 | 40.6 | 4.12 | 14.1 | 0.63 |
| Unk. A1 + Ethanol | 12.7 | 50.0 | 1.09 | 14.6 | 0.06 |
| Unk. A2 + Acetic Acid | 5.0 | 42.2 | 2.77 | 12.6 | 0.57 |

TABLE 10

| Component | NRV (ml) | GRV (ml) | β | Width at Half Height (ml) | R |
|---|---|---|---|---|---|
| Salts & DP3 | 0.0 | 39.9 | 0.00 | 12.6 | 0.86 |
| Lactic Acid | 13.2 | 53.1 | ref. | 18.4 | — |
| B2 + Dextrose | 2.8 | 42.7 | 4.74 | 15.5 | 0.62 |
| A1 + Ethanol | 4.5 | 44.4 | 2.95 | 11.6 | 0.59 |
| A2 + Acetic Acid | 10.6 | 50.5 | 1.25 | 14.6 | 0.17 |

Using the same adsorbent as above, an additional separation of the same 30% lactic acid feed as above was made, at a pH of 1.5 and desorbent concentration of 0.002N H₂SO₄. The results are shown in the following Table 11.

TABLE 11

| Component | NRV (ml) | GRV (ml) | β | Width at Half Height (ml) | R |
|---|---|---|---|---|---|
| Salts & DP3 | 0.0 | 38.2 | 0.00 | 12.2 | 1.0 |
| Lactic Acid | 16.8 | 55.0 | ref. | 21.4 | — |
| B2 + Dextrose | 5.7 | 43.9 | 2.94 | 21.7 | 0.51 |
| Unk. A1 + Ethanol | 4.4 | 42.6 | 3.81 | 13.9 | 0.70 |
| A2(2) + Acetic Acid | 12.2 | 50.4 | 1.37 | 3.8 | 0.36 |

An excellent separation was achieved in each case.

EXAMPLE X

In this example, the same adsorbent was used as in Example IX. The feed was a synthetic lactic acid broth containing 20% (wt.) lactic acid and a deacidified fermentation broth with the following composition:

| Feed Components | wt. % |
|---|---|
| Lactic Acid | 20% |
| Salts | 10% |
| Carbohydrates, Amino Acids and Proteins | 5% |
| Other Impurities and Water | balance |

The desorbent was water. The pH of the feed was 2.5. The results are shown in the following Table 12.

TABLE 12

| Component | NRV (ml) | GRV (ml) | β | Width at Half Height (ml) | R |
|---|---|---|---|---|---|
| Salts | 0.0 | 37.9 | 0.00 | 10.0 | 1.97 |

TABLE 12-continued

| Component | NRV (ml) | GRV (ml) | β | Width at Half Height (ml) | R |
|---|---|---|---|---|---|
| Carbohydrates + Unknown Amino Acids and Proteins | 7.1 | 43.0 | 3.79 | 17.3 | 0.98 |
| Lactic Acid | 26.8 | 64.8 | 1.00 | 23.3 | — |

EXAMPLE XI

Another pulse test was run in the same manner as the preceding pulse tests except as follows: the feed was a synthetic fermentation broth having the following composition:

| Components | Wt. % |
|---|---|
| α Tartaric Acid | 10 |
| NaNO₃ | 10 |
| Glucose | 10 |
| Water | 70 |

Figure 13:
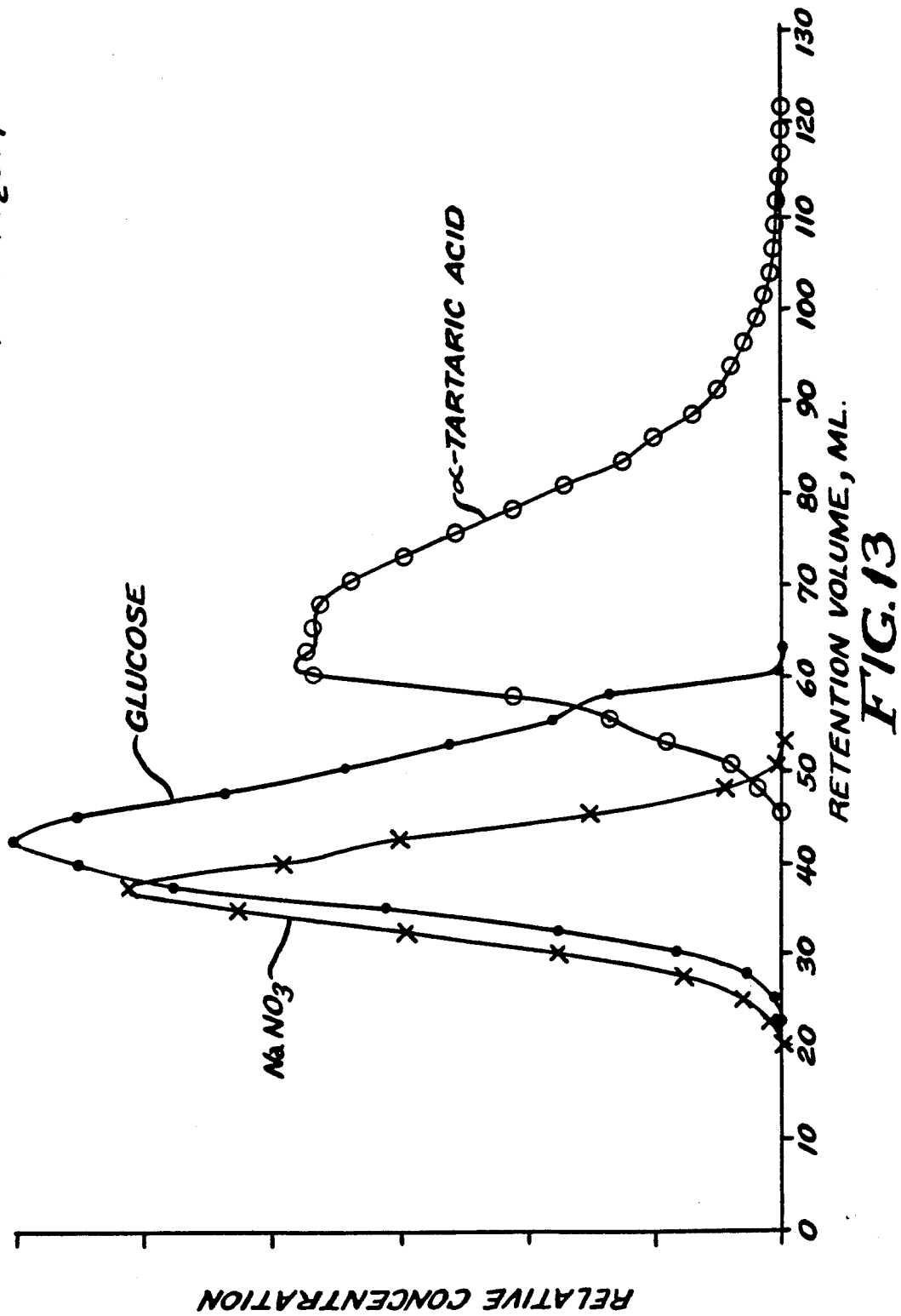
FIG. 13 is the plot of the pulse test of Example XI with a strongly basic anionic exchange resin adsorbent in sulfate form in a crosslinked acrylic resin matrix. The tartaric acid is desorbed with dilute sulfuric acid.

The adsorbent was Amberlite IRA 958 treated as above to convert t to the SO₄⁼ form. The desorbent was 0.1N H₂SO₄ and the pH was 2.1. The results are shown in FIG. 13 and the following Table 13.

TABLE 13

| Component | GRV (ml) | NRV (ml) | β | Width at Half Height (ml) | R |
|---|---|---|---|---|---|
| NaNO₃ | 38.1 | 0.0 | 0.00 | 11.8 | 1.79 |
| Tartaric Acid | 69.0 | 30.9 | 1.00 | 22.8 | — |
| Glucose | 43.7 | 5.7 | 5.45 | 16.7 | 1.28 |

What is claimed is:

1. A process for separating a mono-, di- or polycarboxylic acid from a fermentation broth feed mixture containing said carboxylic acid produced by a fermentation process comprising contacting said feed mixture with an anionic polymeric adsorbent selected from the group consisting of a weakly basic anionic exchange resin possessing tertiary amine or pyridine functional groups and a strongly basic anionic exchange resin possessing quaternary amine functional groups and mixtures thereof at adsorption conditions selected to selectively adsorb said carboxylic acid and thereafter recovering said carboxylic acid from said adsorbent with a desorbent at desorption conditions, said adsorption conditions being characterized as a pH below the first ionization constant (pKa₁) of said carboxylic acid.

2. The process of claim 1 further characterized in that said adsorption and desorption conditions include a temperature within the range of from about 20° C. to about 200° C. and a pressure within the range of from about atmospheric to about 500 psig (3450 kPa gauge).

3. The process of claim 1 further characterized in that said desorption is effected in the liquid phase with water or a dilute inorganic acid.

4. The process of claim 1 further characterized in that said desorbent is 0.002 to 1.0N H₂SO₄.

5. The process of claim 1 further characterized in that the pH of said feed mixture is lower than the ionization constant (pKa) of said carboxylic acid.

6. The process of claim 1 further characterized in that said adsorbent comprises a tertiary amine functional group supported on a matrix comprising a crosslinked acrylic resin.

7. The process of claim 1 further characterized in that said adsorbent comprises a pyridine functional group supported on a matrix selected from the group consisting of polystyrene resins and crosslinked acrylic resins.

8. The process of claim 1 further characterized in that said adsorbent comprises a quaternary ammonium functional group supported on a matrix comprising a crosslinked acrylic resin.

9. The process of claim 1 wherein said adsorbent is in the sulfate form.

10. The process of claim 1 further characterized in that said feed mixture comprises at least one additional material selected from the group consisting of salts, acetic acid, carbohydrates, amino acids and proteins.

11. The process of claim 1 wherein said carboxylic acid is tartaric acid.

12. The process of claim 1 wherein the process is performed in a continuous, countercurrent simulated moving bed system.

13. The process of claim 1 wherein said carboxylic acid is selected from the group consisting of citric acid, lactic acid, aconitic acid, glutamic acid and tartaric acid.

* * * * *